(12) United States Patent
Terpetschnig et al.

(10) Patent No.: US 7,250,517 B2
(45) Date of Patent: Jul. 31, 2007

(54) LUMINESCENT COMPOUNDS

(75) Inventors: Ewald A. Terpetschnig, 22555 Nadine Cir. 239, Torrance, CA (US) 90505; Leonid D. Patsenker, Kharkov (UA); Anatoliy Tatarets, Kharkov (UA)

(73) Assignee: Ewald A. Terpetschnig, Urbana, IL (US)

( * ) Notice: Subject to any disclaimer, the term of this patent is extended or adjusted under 35 U.S.C. 154(b) by 501 days.

(21) Appl. No.: 10/724,580

(22) Filed: Nov. 28, 2003

(65) Prior Publication Data

US 2004/0166515 A1    Aug. 26, 2004

Related U.S. Application Data

(63) Continuation-in-part of application No. 10/396,293, filed on Mar. 24, 2003, now abandoned, which is a continuation-in-part of application No. PCT/US03/10995, filed on Apr. 10, 2003, said application No. 10/396,293 is a continuation-in-part of application No. 09/684,627, filed on Oct. 6, 2000, now Pat. No. 6,538,129, which is a continuation of application No. PCT/US99/07627, filed on Apr. 7, 1999.

(60) Provisional application No. 60/371,832, filed on Apr. 10, 2002, provisional application No. 60/083,820, filed on May 1, 1998.

(30) Foreign Application Priority Data

Apr. 8, 1998    (DE)    ............... 198 15 659.6

(51) Int. Cl.
| C07D 215/12 | (2006.01) |
| C07H 19/04 | (2006.01) |
| C12Q 1/68 | (2006.01) |
| C12Q 1/70 | (2006.01) |
| G01N 33/48 | (2006.01) |
| G01N 21/76 | (2006.01) |

(52) U.S. Cl. .................... 546/176; 536/26.6; 436/172; 436/63; 436/94; 435/5; 435/6

(58) Field of Classification Search ............... 546/176; 436/172, 63, 94; 536/26.6; 435/5, 6
See application file for complete search history.

(56) References Cited

U.S. PATENT DOCUMENTS

| 3,996,345 A | 12/1976 | Ullman et al. |
| 3,998,943 A | 12/1976 | Ullman |
| 4,883,867 A | 11/1989 | Lee et al. |
| 5,101,015 A | 3/1992 | Brynes et al. |
| 5,227,499 A | 7/1993 | McGowan et al. |
| 5,571,388 A | 11/1996 | Patonay et al. |
| 6,083,485 A | 7/2000 | Licha et al. |
| 6,140,494 A | 10/2000 | Hamilton et al. |
| 6,403,807 B1 | 6/2002 | Singh et al. |

FOREIGN PATENT DOCUMENTS

| WO | WO 96/41144 | 12/1996 |
| WO | WO 97/40104 | 10/1997 |

OTHER PUBLICATIONS

*Synthesis and Characterization of Unsymmetrical Squaraines: A New Class of Cyanine Dyes*, Terpetschnig et al., Dyes and Pigments, vol. 21, pp. 227-234, 1993.
*Synthesis, spectral properties and photostabilities of symmetrical and unsymmetrical squaraines; a new class of fluorophores with long-wavelength excitation and emission*, Terpetschnig et al., Analytica Chimica Acta, vol. 282, pp. 633-641, 1993.
*Synthesis of Squaraine-N-Hydroxysuccinimide Esters and Their Biological Application as Long-Wavelength Fluorescent Labels*, Terpetschnig et al., Analytical Biochemistry, vol. 217, pp. 197-204, 1994.
*Synthesis, Spectral Properties, and Detection Limits of Reactive Squaraine Dyes, a New Class of Diode Laser Compatible Fluorescent Protein Labels*, Oswald et al., Bioconjugate Chem., vol. 10, pp. 925-931, 1999.
*Red Laser-Induced Fluorescence Energy Transfer in an Immunosystem*, Oswald et al., Analytical Biochemistry, vol. 280, pp. 272-277, 2000.

Primary Examiner—Jezia Riley
(74) Attorney, Agent, or Firm—Kolisch Hartwell, P.C.

A

B

(57) ABSTRACT

The invention provides reporter compounds based on squaric, croconic, and/or rhodizonic acid, among others, reactive intermediates used to synthesize the reporter compounds, and methods of synthesizing and using the reporter compounds, among others.

The reporter compounds relate generally to the following structure:

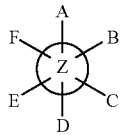

Here, Z is a four, five, or six-member aromatic ring, and A, B, C, D, E, and F are substituents of Z, where F is absent when Z is a five-member ring, and where E and F are absent when Z is a four-member ring.

A, B, C, D, E, and F are selected from a variety of elements and groups, including but not necessarily limited to O, S, Se, Te, N—$R^c$, C($R^f$)($R^g$), $W^1$, and $W^2$

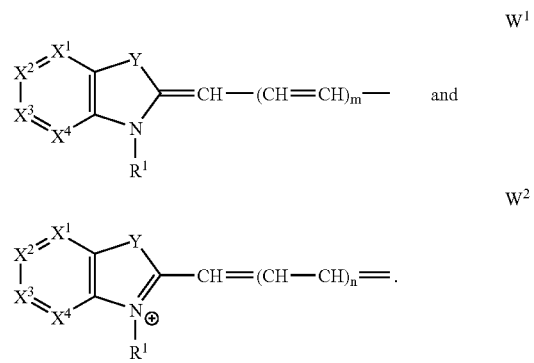

15 Claims, 4 Drawing Sheets

A

B

A

B

LUMINESCENT COMPOUNDS

CROSS-REFERENCES TO PRIORITY APPLICATIONS

This application is continuation-in-part of the following patent applications: U.S. patent application Ser. No. 10/396,293, filed Mar. 24, 2003 now abandoned; and PCT Patent Application Ser. No. PCT/US03/10995, filed Apr. 10, 2003.

U.S. patent application Ser. No. 10/396,293, in turn, is a continuation-in-part of U.S. patent application Ser. No. 09/684,627, filed Oct. 6, 2000, now U.S. Pat. No. 6,538,129, which is a continuation of PCT Patent Application Serial No. PCT/US99/07627, filed Apr. 7, 1999, which is based upon and claims the benefit under 35 U.S.C. §119(e) and all other applicable national and international law of the following patent applications: Deutsches Patentamt Application Ser. No. 198 15 659.6, filed Apr. 8, 1998 in the German Patent Office, entitled REAKTIVE QUADRATSÄURE-UND CROCONSÄURE-FARBSTOFFE ALS MARKER FÜR BIOMOLEKÜLE UND ARZNEISTOFFE, and naming Ewald Terpetschnig as inventor; and U.S. Provisional Patent Application Ser. No. 60/083,820, filed May 1, 1998. U.S. patent application Ser. No. 10/396,293 also is based upon and claims the benefit under 35 U.S.C. §119(e) of U.S. Provisional Patent Application Ser. No. 60/371,832, filed Apr. 10, 2002.

PCT Patent Application Ser. No. PCT/US03/10995, in turn, is based upon and claims the benefit under 35 U.S.C. §119(e) and all other applicable national and international law of U.S. Provisional Patent Application Ser. No. 60/371,832, filed Apr. 10, 2002.

Each of the above-identified U.S., PCT, and foreign priority patent applications is incorporated herein by reference in its entirety for all purposes.

CROSS-REFERENCES TO RELATED MATERIALS

This application incorporates by reference in their entirety for all purposes all patents, patent applications (published, pending, and/or abandoned), and other patent and nonpatent references cited anywhere in this application. The cross-referenced materials include but are not limited to the following publications: Richard P. Haugland, HANDBOOK OF FLUORESCENT PROBES AND RESEARCH CHEMICALS (6$^{th}$ ed. 1996); JOSEPH R. LAKOWICZ, PRINCIPLES OF FLUORESCENCE SPECTROSCOPY (2$^{nd}$ Ed. 1999); RICHARD J. LEWIS, SR., HAWLEY'S CONDENSED CHEMICAL DICTIONARY (12$^{th}$ ed. 1993).

TECHNICAL FIELD

The invention relates to compounds based on squaric, croconic, and/or rhodizonic acid, among others. More particularly, the invention relates to compounds based on squaric, croconic, and/or rhodizonic acid, among others, that are useful as dyes and luminescent reporters.

BACKGROUND

Colormetric and/or luminescent compounds may offer researchers the opportunity to use color and light to analyze samples, investigate reactions, and perform assays, either qualitatively or quantitatively. Generally, brighter, more photostable reporters may permit faster, more sensitive, and more selective methods to be utilized in such research.

While a colorimetric compound absorbs light, and may be detected by that absorbance, a luminescent compound, or luminophore, is a compound that emits light. A luminescence method, in turn, is a method that involves detecting light emitted by a luminophore, and using properties of that light to understand properties of the luminophore and its environment. Luminescence methods may be based on chemiluminescence and/or photoluminescence, among others, and may be used in spectroscopy, microscopy, immunoassays, and hybridization assays, among others.

Photoluminescence is a particular type of luminescence that involves the absorption and subsequent re-emission of light. In photoluminescence, a luminophore is excited from a low-energy ground state into a higher-energy excited state by the absorption of a photon of light. The energy associated with this transition is subsequently lost through one or more of several mechanisms, including production of a photon through fluorescence or phosphorescence.

Photoluminescence may be characterized by a number of parameters, including extinction coefficient, excitation and emission spectrum, Stokes' shift, luminescence lifetime, and quantum yield. An extinction coefficient is a wavelength-dependent measure of the absorbing power of a luminophore. An excitation spectrum is the dependence of emission intensity upon the excitation wavelength, measured at a single constant emission wavelength. An emission spectrum is the wavelength distribution of the emission, measured after excitation with a single constant excitation wavelength. A Stokes' shift is the difference in wavelengths between the maximum of the emission spectrum and the maximum of the absorption spectrum. A luminescence lifetime is the average time that a luminophore spends in the excited state prior to returning to the ground state. A quantum yield is the ratio of the number of photons emitted to the number of photons absorbed by a luminophore.

Luminescence methods may be influenced by extinction coefficient, excitation and emission spectra, Stokes' shift, and quantum yield, among others, and may involve characterizing fluorescence intensity, fluorescence polarization (FP), fluorescence resonance energy transfer (FRET), fluorescence lifetime (FLT), total internal reflection fluorescence (TIRF), fluorescence correlation spectroscopy (FCS), fluorescence recovery after photobleaching (FRAP), and their phosphorescence analogs, among others.

Luminescence methods have several significant potential strengths. First, luminescence methods may be very sensitive, because modern detectors, such as photomultiplier tubes (PMTs) and charge-coupled devices (CCDs), can detect very low levels of light. Second, luminescence methods may be very selective, because the luminescence signal may come almost exclusively from the luminophore.

Despite these potential strengths, luminescence methods may suffer from a number of shortcomings, at least some of which relate to the luminophore. For example, the luminophore may have an extinction coefficient and/or quantum yield that is too low to permit detection of an adequate amount of light. The luminophore also may have a Stokes' shift that is too small to permit detection of emission light without significant detection of excitation light. The luminophore also may have an excitation spectrum that does not permit it to be excited by wavelength-limited light sources, such as common lasers and arc lamps. The luminophore also may be unstable, so that it is readily bleached and rendered nonluminescent. The luminophore also may have an excitation and/or emission spectrum that overlaps with the well-known autoluminescence of biological and other samples; such autoluminescence is particularly significant at wavelengths below about 600 nm. The luminophore also may be expensive, especially if it is difficult to manufacture.

SUMMARY

The invention provides reporter compounds based on squaric, croconic, and/or rhodizonic acid, among others, reactive intermediates used to synthesize the reporter compounds, and methods of synthesizing and using the reporter compounds, among others.

The reporter compounds relate generally to the following structure:

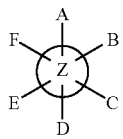

Here, Z is a four, five, or six-member aromatic ring, and A, B, C, D, E, and F are substituents of Z, where F is absent when Z is a five-member ring, and where E and F are absent when Z is a four-member ring. Generally, A, B, C, D, E, and F may be present in any order, although the order may be limited in certain embodiments.

A, B, C, D, E, and F are selected from a variety of elements and groups, including but not necessarily limited to O, S, Se, Te, N—$R^c$, $C(R^f)(R^g)$, $W^1$, and $W^2$.

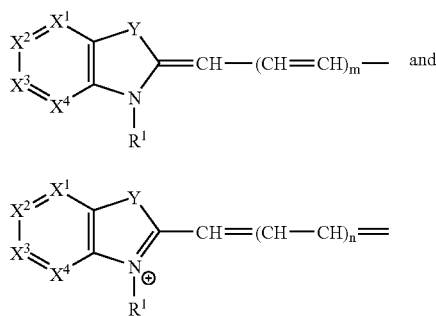

The components $R^a$, $R^b$, $R^c$, $R^d$, $R^e$, n, m, $X^1$, $X^2$, $X^3$, $X^4$, and Y are defined in detail in the Detailed Description. However, generally, each compound includes at least one of $W^1$ or $W^2$, With the preferred synthetic precursors including one, and the preferred reporter compounds including two. The compound may include at least one S. Alternatively, or in addition, the compound may include at least one heteroatom in $X^1$ through $X^4$ of $W^1$ or $W^2$. Alternatively, or in addition, the compound may include a reactive group and/or a carrier. Alternatively, or in addition, A, B, C, D, E, and F may be chosen so that the compound is photoluminescent.

The methods relate generally to the synthesis and/or use of reporter compounds, especially those described above.

The nature of the invention will be understood more readily after consideration of the drawing, chemical structures, and detailed description that follow.

ABBREVIATIONS

Figure 1:
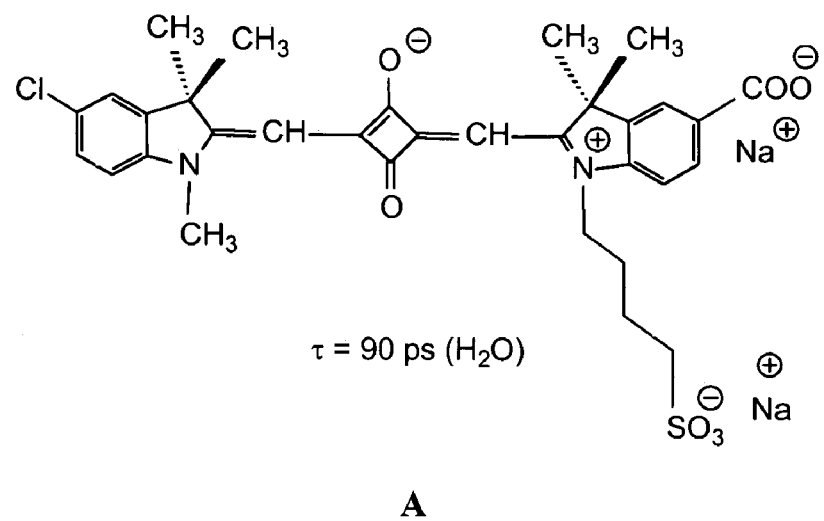
FIG. 1 compares the fluorescence lifetimes of squaraine dyes A and B having different numbers of ionic substituents.
Figure 1:
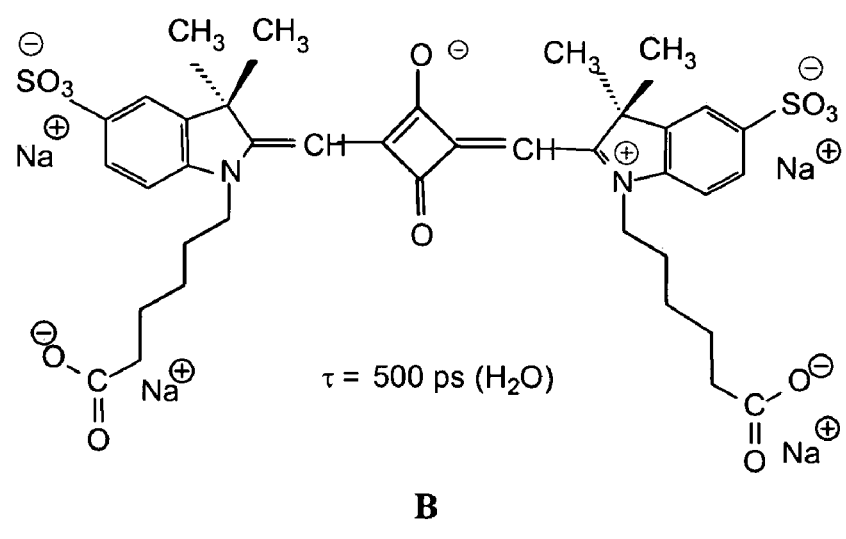

The following abbreviations, among others, may be used in this application:

| Abbreviation | Definition |
| --- | --- |
| BSA | bovine serum albumin |
| Bu | butyl |
| DCC | dicyclohexylcarbodiimide |
| DMF | dimethylformamide |
| D/P | dye-to-protein ratio |
| Et | ethyl |
| g | grams |
| h | hours |
| HSA | human serum albumin |
| hCG | human chorionic gonadotropin |
| L | liters |
| m | milli ($10^{-3}$) |
| M | molar |
| Me | methyl |
| mol | moles |
| M.P. | melting point |
| n | nano ($10^{-9}$) |
| NHS | N-hydroxysuccinimide |
| NIR | near infrared region |
| PBS | phosphate-buffered saline |
| Prop | propyl |
| TMS | tetramethylsilane |
| TSTU | N,N,N',N'-tetramethyl(succinimido) uronium tetrafluoroborate |
| μ | micro ($10^{-6}$) |

DETAILED DESCRIPTION OF THE INVENTION

The invention relates generally to photoluminescent compounds and their synthetic precursors, and to methods of synthesizing and using such compounds. These photoluminescent compounds may be useful in both free and conjugated forms, as probes, labels, and/or indicators. This usefulness may reflect in part enhancement of one or more of the following: quantum yield, Stokes' shift, extinction coefficients, and photostability. This usefulness also may reflect excitation and emission spectra in relatively inaccessible regions of the spectrum, including the red and near infrared.

The remaining discussion includes (1) an overview of structures, (2) an overview of synthetic methods, and (3) a series of illustrative examples.

Overview of Structures

The reporter compounds and their synthetic precursors may be generally described by the following structure:

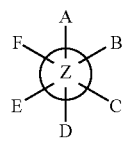

Here, Z is a four, five, or six-member aromatic ring, and A, B, C, D, E, and F are substituents of Z, where F is absent if Z is a five-member ring, and where E and F are absent if Z is a six-member ring. A, B, C, D, E, and F may be singly or doubly bonded to Z.

Ring Z may take a variety of forms. Preferred rings are based on four-member squaric acid, five-member croconic acid, and six-member rhodizonic acid, and/or their analogs, with substitutions as described below.

Substituents A, B, C, D, E, and F also may take a variety of forms. Preferred substituents include O, S, Se, Te, N—$R^c$, $C(R^f)(R^g)$, $W^1$, and $W^2$. $R^c$ may be selected from the group consisting of aliphatic, heteroatom-substituted aliphatic, polyether, aromatic, reactive aliphatic, and reactive aromatic groups, among others. $R^f$ and $R^g$ may be selected from the group consisting of carboxylic acid, cyano, carboxamide, carboxylic ester, and aliphatic amine groups, among others. Alternatively, or in addition, $R^f$ and $R^g$, taken in combination, may form 5- and 6-membered rings.

$W^1$ and $W^2$ may include the following structures, among others:

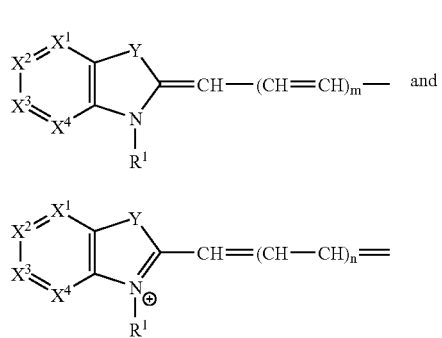

For each of $W^1$ and $W^2$, the variables n, m, Y, $R^1$, and $X^1$ through $X^4$ generally may be defined independently, as follows. The integers n and m may independently be 0, 1, or 2. Y may be O, S, Se, Te, N—$R^f$, and $C(R^g)(R^h)$. $R^f$ may be H, aliphatic groups, alicyclic groups, aromatic groups, and reactive aliphatic groups, among others. $R^g$ and $R^h$ may be aliphatic and reactive aliphatic groups, among others. $R^1$ may be H, aliphatic groups, alicyclic groups, aromatic groups, linked carriers, reactive groups capable of covalent attachment to a carrier, spacers bound to one or more reactive groups capable of covalent attachment to a carrier, and ionic substituents capable of increasing the hydrophilicity of the entire compound, among others. Finally, ring members $X^1$, $X^2$, $X^3$, and $X^4$ may be selected from N, O, S, and C—$R^i$, where $R^i$ may be H, aliphatic groups, alicyclic groups, aromatic groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring, among others. The substituents on the substituted rings may be chosen quite broadly, and may include the various component listed above, among others.

Reporter Compounds

Where the reporter compound is a colorimetric dye and/or a photoluminescent compound, B and C are typically chosen from $W^1$ and/or $W^2$, and A, B, C, D, E, and F typically are present in any order. If B and C are adjacent, then each of B and C is $W^1$, and each of A, D, E, and F is neutral. If B and C are separated by one of A, D, E, or F, then one of B and C is $W^1$, one of B and C is $W^2$, and one of A, D, E, and F is negatively charged. If B and C are separated by two of A, D, E, and F, which is possible only in the six-member ring, then each of B and C is $W^2$, and each of A, D, E, and F is neutral.

Representative structures for the reporter compounds are shown below, where $W^1$ and $W^2$ represent the structures defined above, and where $V^1$ through $V^4$ represent the structures A, D, E, and F as defined above, in any order.

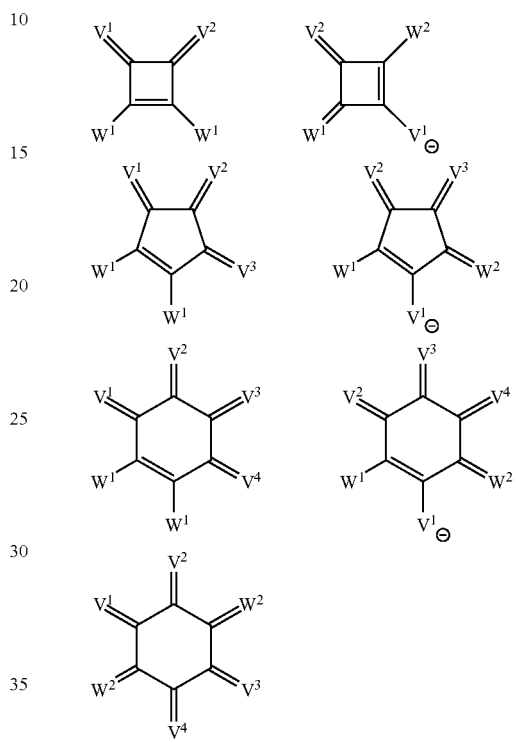

Depending on the embodiment, A, B, C, D, E, and F may be subject to additional limitations. In some embodiments, the compound also includes at least one of S, Se, Te, and $C(R^a)(R^b)$. In other embodiments, at least one of $X^1$ through $X^4$ of $W^1$ or $W^2$ is or includes a heteroatom. In yet other embodiments, the compound may include a reactive group and/or a carrier. The reporter compounds may be colorimetric dyes, useful as stains and for colorimetric detection. Alternatively or in addition, the reporter compounds may be photoluminescent, particularly fluorescent, and may have utility in photoluminescence assays and methods, as discussed above.

Synthetic Precursors.

Were the compound has utility as a synthetic precursors, B typically is one of $W^1$ and $W^2$, and C is analogous to D, E, and F. A representative precursor in which Z is a four-member ring is shown below.

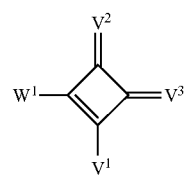

Here, $V^1$ may be $O^-$, $S^-$, OH, SH, OR, SR, NRH, NRR (where each R is independently methyl, ethyl, i-propyl, butyl, among others); and $[C(R')(R')]^-$, among others, where each R' may be CN, COOH, C(=O)NHR, COOEt, COOCH$_3$, among others. $V^2$ and $V^3$ may be O, S, NR, and CRR, among others, where each R may be CN, COOH, C(=O)NHR, and COOEt, aliphatic and aromatic groups, among others.

Analogous precursors in which Z is a five or six-member ring also may be useful as synthetic precursors. Examples of selected compounds and their synthetic routes are shown below:

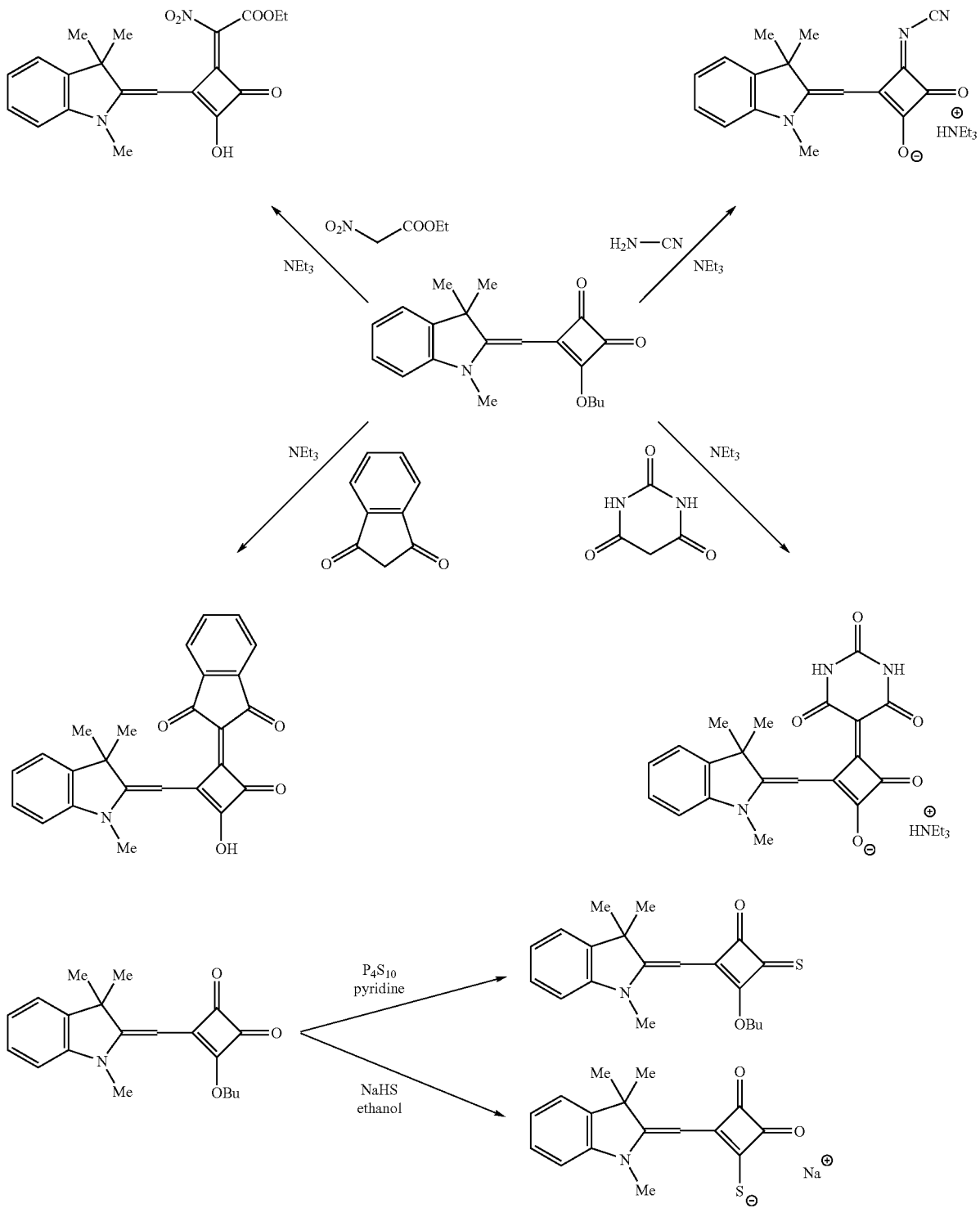

Tandems.

Reporter compounds in accordance with the invention also may include pairs, triplets, and higher numbers of compounds conjugated together to form a single compound. Such "tandems" may be used to obtain alternative spectral properties, such as enhanced Stokes' shifts. Such tandems also may be Used in energy transfer, or for other purposes. Some potential combinations are drawn below, where A, B, C, D, E, F, and Z have their usual meanings, and U represents a cross-link, such as may be formed by cross-reaction using a reactive compound. Z and each substituent may be chosen independently for each component of a tandem.

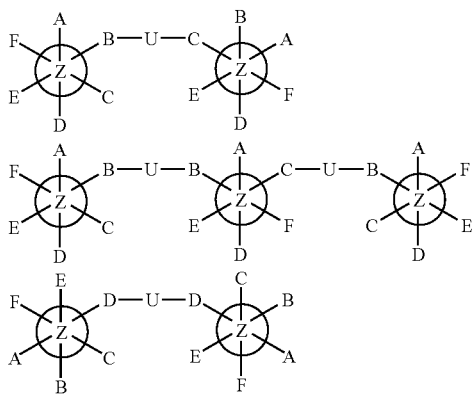

Reactive Groups.

The substituents of Z may include one or more reactive groups, where a reactive group generally is a group capable of forming a covalent attachment With another molecule or substrate. Such other molecules or substrates may include proteins, carbohydrates, nucleic acids, and plastics, among others. Reactive groups vary in their specificity, and may preferentially react with particular functionalities and molecule types. Thus, reactive compounds generally include reactive groups chosen preferentially to react with fundtionalities found on the molecule or substrate with which the reactive compound is intended to react.

The compounds Of the invention are optionally substituted, either directly or via a substituent, by one or more chemically reactive functional groups that may be useful for covalently attaching the compound to a desired substance. Each reactive group, or $R_x$, may be bound to the compound directly by a single covalent bond, or may be attached via a covalent spacer or linkage, L, and may be depicted as —L—$R_x$.

The reactive functional group of the invention may be selected from the following functionalities, among others: activated carboxylic esters, acyl azides, acyl halides, acyl halides, acyl nitriles, acyl nitriles, aldehydes, ketones, alkyl halides, alkyl sulfonates, anhydrides, aryl halides, azindines, boronates, carboxylic acids, carbodiimides, diazoalkanes, epoxides, haloacetamides, halotriazines, imido esters, isocyanates, isothiocyanates, maleimides, phosphoramidites, silyl halides, sulfonate esters, and sulfonyl halides.

In particular, the following reactive functional groups, among others, are particularly useful for the preparation of labeled molecules or substances, and are therefore suitable reactive functional groups for the purposes of the reporter compounds:

a) N-hydroxysuccinimide esters, isothiocyanates, and sulfonylchlorides, which form stable covalent bonds with amines, including amines in proteins and amine-modified nucleic acids;
b) Iodoacetamides and maleimides, which form covalent bonds with thiol-functions, as in proteins;
c) Carboxyl functions and various derivatives, including N-hydroxybenztriazole esters, thioesters, p-nitrophenyl esters, alkyl, alkenyl, alkynyl, and aromatic esters, and acyl imidazoles;
d) Alkylhalides, including iodoacetamides and chloroacetamides;
e) Hydroxyl groups, which can be converted into esters, ethers, and aldehydes;
f) Aldehydes and ketones and various derivatives, including hydrazones, oximes, and semicarbozones;
g) Isocyanates, which may react with amines;
h) Activated C=C double-bond-containing groups, which may react in a Diels-Alder reaction to form stable ring systems under mild conditions;
i) Thiol groups, which may form disulfide bonds and react with alkylhalides (such as iodoacetamide);
j) Alkenes, which can undergo a Michael addition with thiols, e.g., maleimide reactions with thiols;
k) Phosphoramidites, which can be used for direct labeling of nucleosides, nucleotides, and oligonucleotides, including primers on solid or semi-solid supports;
l) Primary amines that may be coupled to variety of groups including carboxyl, aldehydes, ketones, and acid chlorides, among others; and
m) Boronic acid derivatives that may react with sugars.

R Groups.

The R moieties associated with the various substituents of Z may include any of a number of groups, as described above, including but not limited to alicyclic groups, aliphatic groups, aromatic groups, and heterocyclic rings, as well as substituted versions thereof.

Alicyclic groups include groups of organic compounds characterized by an arrangement of the carbon atoms in a closed ring structure that may resemble a boat, a chair, or even a bird cage. These compounds have properties resembling those of aliphatics and should not be confused with aromatic compounds having the hexagonal benzene ring. Alicyclics may comprise three subgroups: (1) cycloparaffins (saturated), (2) cycloolefins (unsaturated with two or more double bonds), and (3) cycloacetylenes (cyclynes) with a triple bond. The best-known cycloparaffins (sometimes called naphthenes) are cyclopropane, cyclohexane, and cyclopentane; typical of the cycloolefins are cyclopentadiene and cyclooctatetraene. Most alicyclics are derived from petroleum or coal tar, and many can be synthesized by various methods.

Aliphatic groups may include groups of organic compounds characterized by straight- or branched-chain arrangement of the constituent carbon atoms. Aliphatic hydrocarbons comprise three subgroups: (1) paraffins (alkanes), which are saturated and comparatively unreactive; (2) olefins (alkenes or alkadienes), which are unsaturated and quite reactive; and (3) acetylenes (alkynes), which contain a triple bond and are highly reactive. In complex structures, the chains may be branched or cross-linked and may contain one or more heteroatoms (such as polyethers and polyamines, among others).

Aromatic groups may include groups of unsaturated cyclic hydrocarbons containing One or More rings. A typical aromatic group is benzene, which has a 6-carbon ring formally containing three double bonds in a delocalized ring system. Aromatic groups may be highly reactive and chemically versatile. Most aromatics are derived from petroleum and coal tar. Heterocyclic rings include closed-ring structures, usually of either 5 or 6 members, in which one or more of the atoms in the ring is an element other than carbon, e.g., sulfur, nitrogen, etc. Examples include pyridine, pyrole, furan, thiophene, and purine. Some 5-membered heterocyclic compounds exhibit aromaticity, such as furans and thiophenes, among others, and are analogous to aromatic compounds in reactivity and properties.

Carriers and Conjugated Substances.

The reporter compounds of the invention, including synthetic precursor compounds, may be covalently or noncovalently associated with one or more substances. Covalent association may occur through various mechanisms, including a reactive functional group as described above, and may involve a covalent linkage, L, separating the compound or precursor from the associated substance (which may therefore be referred to as —L—$S_c$).

Where the substance is associated noncovalently, the association may occur through various mechanisms, including incorporation of the compound or precursor into or onto a solid or semisolid matrix, such as a bead or a surface, or by nonspecific interactions, such as hydrogen bonding, ionic bonding, or hydrophobic interactions (such as Van der Waals forces). The associated carrier may be selected from the group consisting of polypeptides, polynucleotides, polysaccharides, beads, microplate well surfaces, metal surfaces, semiconductor and non-conducting surfaces, nano-particles, and other solid surfaces.

The associated or conjugated substance may be associated with or conjugated to more than one reporter compound, which may be the same or different. Generally, methods for the preparation of dye-conjugates of biological substances are well-known in the art. See, for example, Haugland et al., MOLECULAR PROBES HANDBOOK OF FLUORESCENT PROBES AND RESEARCH CHEMICALS, Eighth Edition (1996), which is hereby incorporated by reference. Typically, the association or conjugation of a chromophore or luminophore to a substance imparts the spectral properties of the chromophore or luminophore to that substance.

Useful substances for preparing conjugates according to the present invention include, but are not limited to, amino acids, peptides, proteins, nucleosides, nucleotides, nucleic acids, carbohydrates, lipids, ion-chelators, nonbiological polymers, cells, and cellular components. The substance to be conjugated may be protected on one or more functional groups in order to facilitate the conjugation, or to insure subsequent reactivity.

Where the substance is a peptide, the peptide may be a dipeptide or larger, and typically includes 5 to 36 amino acids. Where the conjugated substance is a protein, it may be an enzyme, an antibody, or a phycobiliprotein. The conjugated substance may be a nucleic acid polymer, such as for example DNA oligonucleotides, RNA oligonucleotides (or hybrids thereof), or single-stranded, double-stranded, triple-stranded, or quadruple-stranded DNA, or single-stranded or double-stranded RNA. One class of carriers includes carbohydrates that are polysaccharides, such as dextrans.

Where the substance is an ion chelator, the resulting conjugate may be useful as an ion indicator, particularly where the optical properties of the reporter-conjugate are altered by binding a target ion.

The associated or conjugated substance may be a member of a specific binding pair, and therefore useful as a probe for the complementary member of that specific binding pair, each specific binding pair member having an area on the surface or in a cavity which specifically binds to and is complementary with a particular spatial and polar organization of the other. The conjugate of a specific binding pair member may be useful for detecting and optionally quantifying the presence of the complementary specific binding pair member in a sample, by methods that are well known in the art.

Representative specific binding pairs may include ligands and receptors, and may include but are not limited to the following pairs: antigen-antibody, biotin-avidin, biotin-streptavidin, IgG-protein A, IgG-protein G, carbohydrate-lectin, enzyme-enzyme substrate; DNA-antisense DNA, and RNA-antisense RNA.

Preferably, the associated or conjugated substance includes proteins, carbohydrates, nucleic acids, and nonbiological polymers such as plastics, metallic nanoparticles such as gold, silver and carbon nanostructures among others.

Synthesis and Characterization

The synthesis of the disclosed reporter compounds typically is achieved in a multi-step reaction, starting with the synthesis of a methylene base. The synthesis of suitable bases may proceed based on literature or novel methods. Generally, the spectral properties of the reporter compounds, including excitation and emission wavelengths for luminescent compounds, may be strongly dependent on the type of methylene base used. Typical starting materials include benzindoles, benzoselenzoles, benzoxazoles, benzimidazoles, etc., and squaric acid.

Other starting materials may contain additional spacer groups in position 3 of the indolenine ring. The introduction of spacer groups and/or increasing the number of sulfonate groups may help to reduce the tendency of the dyes to aggregate in aqueous solution and when covalently bound to proteins.

Conjugates of dyes as described in Examples 12–14 with proteins and other biomolecules might exhibit higher quantum yields at higher dye-to-protein ratios. Such effects and the synthesis of compounds 1d to 1f from 2-methyl acetoacetate are described in U.S. Patent Application Publication No. 2002/0077487 A1, which is hereby incorporated by reference.

Squaric acid is a dibasic acid that undergoes a series of nucleophilic substitution reactions with various reagents, including amines, phenols, and CH-acidic compounds such as 1,2,3,3-tetramethyl-benzindole. The squaraine bridge in the resulting compounds stabilizes the conjugated chain and shifts the excitation and emission wavelength of these dyes to the red as compared to cyanine-based dyes. In particular, the exchange of the oxygen in the squaraine moiety by an imino (=N—R), sulfur or a methylene (=$CR_2$) moiety is shown here to be a pathway to useful reporter molecules with advantageous fluorescence properties.

In the following examples, the synthesis and spectral characterization of several long-wavelength reporter compounds based on squaraine and other dyes is presented, including some reactive versions. These dyes may include a cyanine-type chromophore and a squarate bridge. To enhance water-solubility, sulfonic acid or other groups such as including quaternary ammonium, polyether, carboxyl, and phosphate, among others, may be introduced into the heterocyclic ring systems. In order to facilitate covalent attachment to proteins, reactive N-hydroxy-succinimide ester (NHS ester) or other forms may be synthesized. To modify the spectral properties of the reporter compounds, sulfo-, imino- and dicyanomethylene-substituted versions of the squaraines were prepared, and subsequently tested for their potential use for labeling of biopolymers.

In general the squaraine-based markers exhibit low quantum yields in water ($\phi$=0.05–0.15) and very high quantum yields ($\phi$=0.2–0.7) when bound to biomolecules. The absorption and emission wavelengths of the reporter compounds may be tuned by substitution of the squaraine ring, by introducing heteroatoms into the heterocyclic moiety and by increasing the length of the conjugated carbon chain. Thus, the indolenine-squaraines and thiosquaraines absorb around 635 nm to 650 nm in water and at approximately 645 to 660 nm when bound to proteins. The absorption and emission spectra of benzothiazolium and benzoselenzolium squaraines are shifted towards longer wavelengths. The emission maxima for benzothiazole based squaraine dyes in organic solvents are around 680 nm to 690 nm and beyond 700 nm for benzoselenzole derivatives. Importantly, the Stokes' shift increases in these longer wavelength-emitting dyes, which ultimately increases the sensitivity of a fluorescent measurement.

The resulting dyes show absorption and emission maxima starting at about 500 to beyond about 800 nm, and these wavelengths may be tuned by changing the heterocyclic moiety and/or the substituents on the central squaraine ring. The Stokes' shift of the sulfur or methylene derivatives of symmetric squaraines (9), (13), and (15) may be increased more than 2.5 times relative to the Stokes' shift of the analogous oxygen-containing squaraines (8) and (3b). In addition, the replacement of C=O by C=C or C=S in example (15) or example (9) results in a bathochromic shift of both, the absorption and the emission properties of these dyes. A further increase of the Stokes' shift may be achieved by introducing asymmetry into the molecule. Thus, the asymmetric versions (13) and (15) are expected to have even higher Stokes' shifts.

Various methods may be used for synthesizing dithiosquaraine dyes: In one approach, dithio-squaraine dyes are synthesized from their oxygen analogs, using $P_4S_{10}$ as a reagent.

In another synthetic approach, as described in Example 5, dithiosquaraine dyes are synthesized using a 1,3,3-trimethyl-2-indolinylidene methyl-substituted squaraine that is allowed to react with $P_4S_{10}$. The dithiosquaraine could be synthesized in sufficient yield using 1.2 equivalents of $P_4S_{10}$. Importantly, elemental analysis and absorption and emission spectral data used to characterize the reaction product showed bright emission with a Stokes' shift of 49 nm in chloroform.

In yet another approach, an asymmetric squaraine dye was synthesized and reacted with $P_4S_{10}$ using pyridine as solvent. After reacting the squaric acid compound with $P_4S_{10}$, a new long-wavelength emitting compound was isolated. The absorption and emission spectral properties were clearly distinguishable from those of the parent oxo-derivative. The exchange of oxygen for sulfur in dye (11) led to a 14-nm increase of the Stokes' shift, resulting in a total shift of 37 nm. An increased Stokes' shift may result in improved sensitivity for fluorescence measurements, due to better separation of the excitation and emission maxima, permitting the molecules to be excited at their absorbance maximum, rather than at shorter wavelengths with lower extinction coefficients.

All attempts to synthesize the thio-analogues of sulfonato-squaraine derivatives directly using $P_4S_{10}$ or Lawessons Reagent failed. A number of deep blue colored products were obtained, but their purification appeared to be very difficult. The route using dithiosquaric acid disodium salt as a starting material appeared to be more successful. This starting material was synthesized in a two-step reaction from squaric acid using DMF and aminophenol and subsequently sodium hydrogen sulfide as reagents. Using dithiosquaric acid as starting material, the dithio-analogue of the symmetric squaraine dye (13) was synthesized and characterized using $^1$H-NMR, absorption and emission spectral data. The reaction controlled by TLC clearly shows two products with different $R_f$ values: $R_f$: 0.75 for the diacid (13) and a minor spot with an $R_f$: 0.55 presumably for the dibutylester which is due to the esterification of the $\epsilon$-carboxylic acid functions in BuOH. In contrast to the thiosquaric acid, the dibutylester formation is preferred in the dioxo-squaraine synthesis pathway, and thus the ester is the main product. The spectral properties of the thiosquaraine dye remain very similar to its dioxo-analogue.

The substitution of one oxygen or sulfur of the central squarate bridge with CH-acidic reagents e.g. dicyanomethane, HOOC—$(CH_2)$—COOH, or ROOC—$(CH_2)$—CN leads to the group of luminescent methylenesquaraine derivatives. As compared to the basic squaraines these compounds have red-shifted excitation and emission properties and larger Stokes' shifts. The absorption and emission maxima of a representative reactive dye (15) (example 7) were found to be 667 nm and 685 nm in PBS, respectively.

Example 8 demonstrates the conversion of a croconium dye into a reactive protein label. Croconium dyes are cyanine dyes which contain a five-member central croconium bridge. As compared to cyanine dyes the croconium bridge shifts the excitation and emission wavelength of these dyes about 100 nm to the red and improves their photostability. The excitation and emission wavelengths of a substituted benzothiazolium croconium dye in methanol was measured be 750 nm and 788 nm, respectively. The conversion of a sulfonated croconium dye into a reactive sulfonyl chloride derivative was achieved by reaction of the dye with $PCl_5$ and subsequent extraction of the reactive dye into $CHCl_3$.

Example 9 describes synthetic pathways to unsymmetrical thiosquaraine and methylene-squaraine dyes. The key intermediates for these types of squaraine dyes are mono-substituted thiosquaraine and methylene-squaraine derivatives synthesized from the oxo-derivative 18, as described in the following patent applications, which are hereby incorporated by reference: Japanese Patent Application JP2000285978; and PCT Patent Application Ser. No. PCT/US03/10995, filed Apr. 10 2003. Subsequently, these intermediates are reacted with one equivalent of a different methylene base. The synthesis of unsymmetrical squaraine dyes allows access to mono-functional reactive squaraine dyes, that show improved labelling performance and reduced crosslinking with proteins.

Examples 10 and 11 describe the synthesis of novel imino-substituted squaraine dyes, such as structure 20 below. These imino-squaraines have not been synthesized and reported in the literature previously:

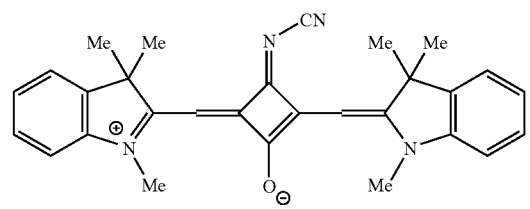

20

-continued

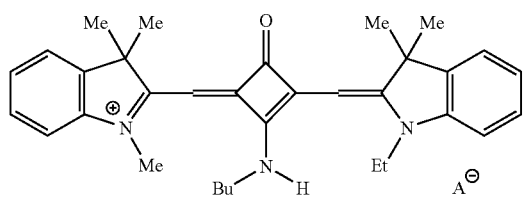

7e

While similar dyes have been described previously (see, for example, U.S. Pat. No. 6,140,494 to Hamilton et al.; and Dyes and Pigments 37, 145–154, 1998, both of which are hereby incorporated by reference), such dyes are cationic dyes that have a positive net charge and a negative counter ion (see 7e, above). Reporter compounds such as 20 are neutral with a negative charge on the central squaraine ring and a positive charge on the indolenine-nitrogen. Compounds such as 20 typically have only one substituent on the squaraine-nitrogen, while compounds such as 7e always have 2 substituents on this nitrogen. Due to the "vinylogous amide" nature of compounds like 7e it is not possible to easily remove the proton on this "amide nitrogen" and to convert compounds such as 7e to compounds of structure 20. They can only be synthesized using the novel route described in examples 10 and 11 in this application.

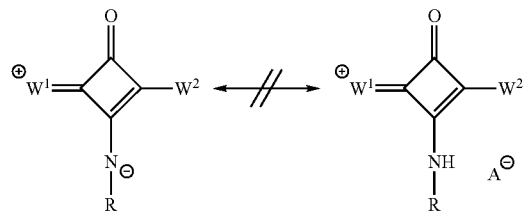

In addition, neutral compounds such as 20 are preferred for encapsulation in beads (polystyrene) while cationic compounds such as 7e only give low incorporation yields.

Preferred embodiments of imino-squaraine dyes have the following substituents on the squaraine-ring nitrogen atom ($R_c$=OH, CN, COOR, COOH, $SO_3H$ etc.):

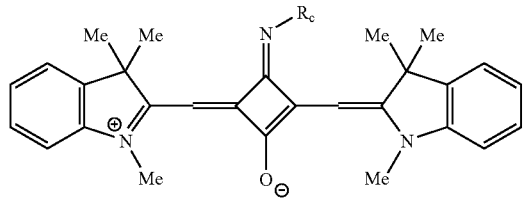

The reporter compounds shown in Examples 12–15 include a new position available for covalent association and/or introducing an ionic substituent and a linker (spacer) in order to increase the water-solubility and to reduce the aggregation tendency of the entire molecule (see below).

Examples 12 and 13 describe the synthesis of symmetrical and unsymmetrical squaraine dyes that contain a linker (spacer) group including a new labeling position in position 3.

The novel branched squaraine dyes might also help to improve the shortcomings of common squaraine dyes such as short lifetimes and low quantum yields in aqueous solution. The short lifetime and low quantum yields can mostly be attributed to quenching and aggregation of dye molecules in aqueous solution. By changing the structure and introducing a larger number of sulfonate or other ionic groups, optionally including spacers, the tendency of these labels for self-aggregation and quenching can be reduced. A correlation between water-solubility and the fluorescence lifetime can be seen in FIG. 1.

Figure 2:
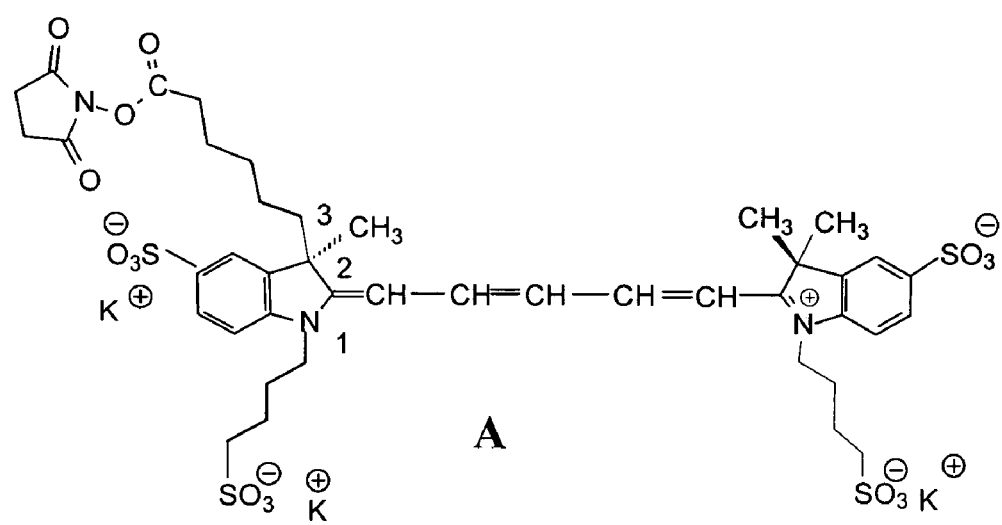
FIG. 2 provides chemical structures of an ALEXA Dye Series NHS ester (A) and a CY5NHS ester (B).
Figure 2:
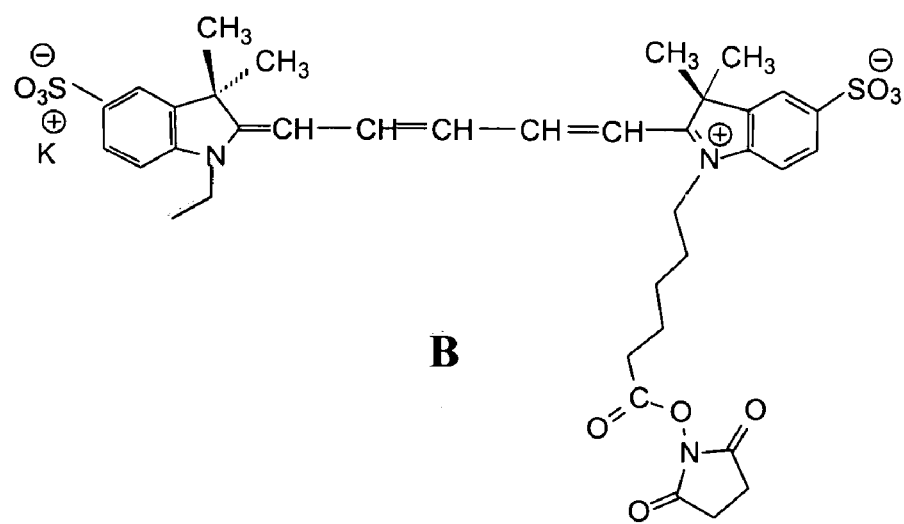
Figure 3:
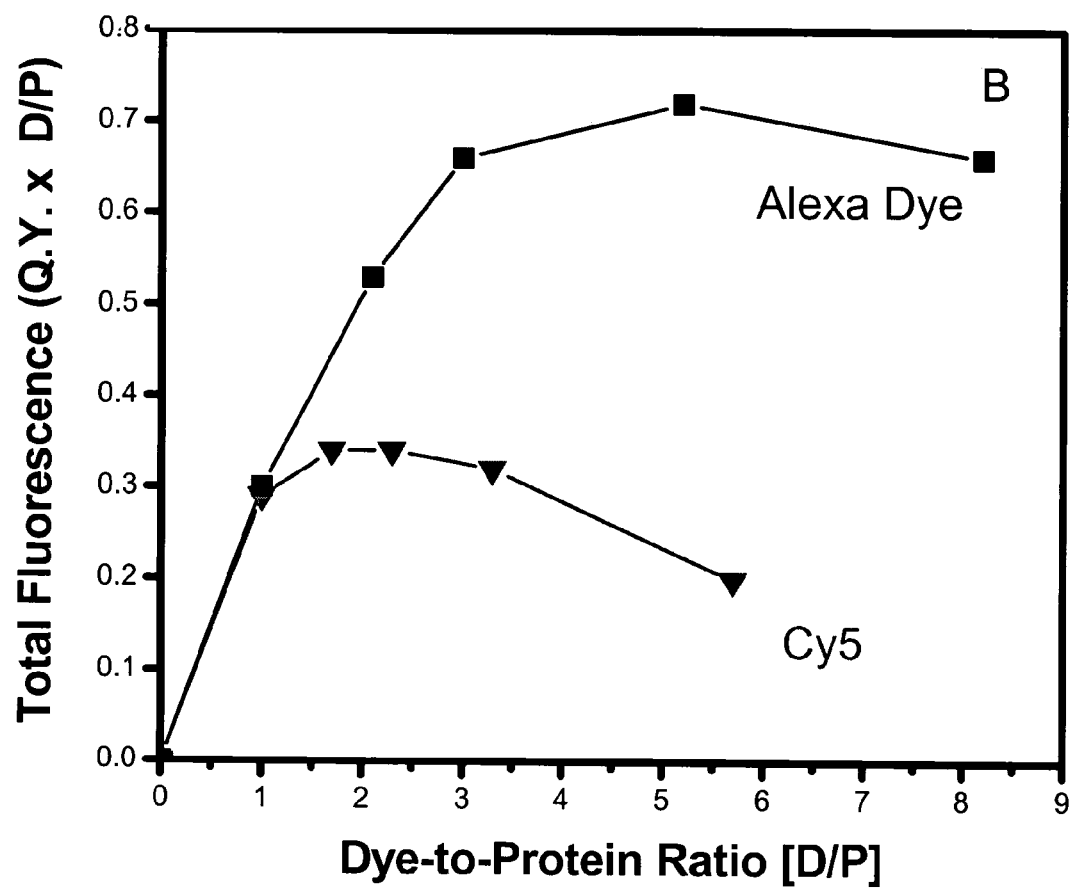
FIG. 3 compares the total fluorescence of IgG-conjugates of CY5 dye (▼) and an ALEXA dye (■) as a function of dye-protein ratio (see U.S. Patent Application Publication No. 2002/0077487 A1).
Figure 4:
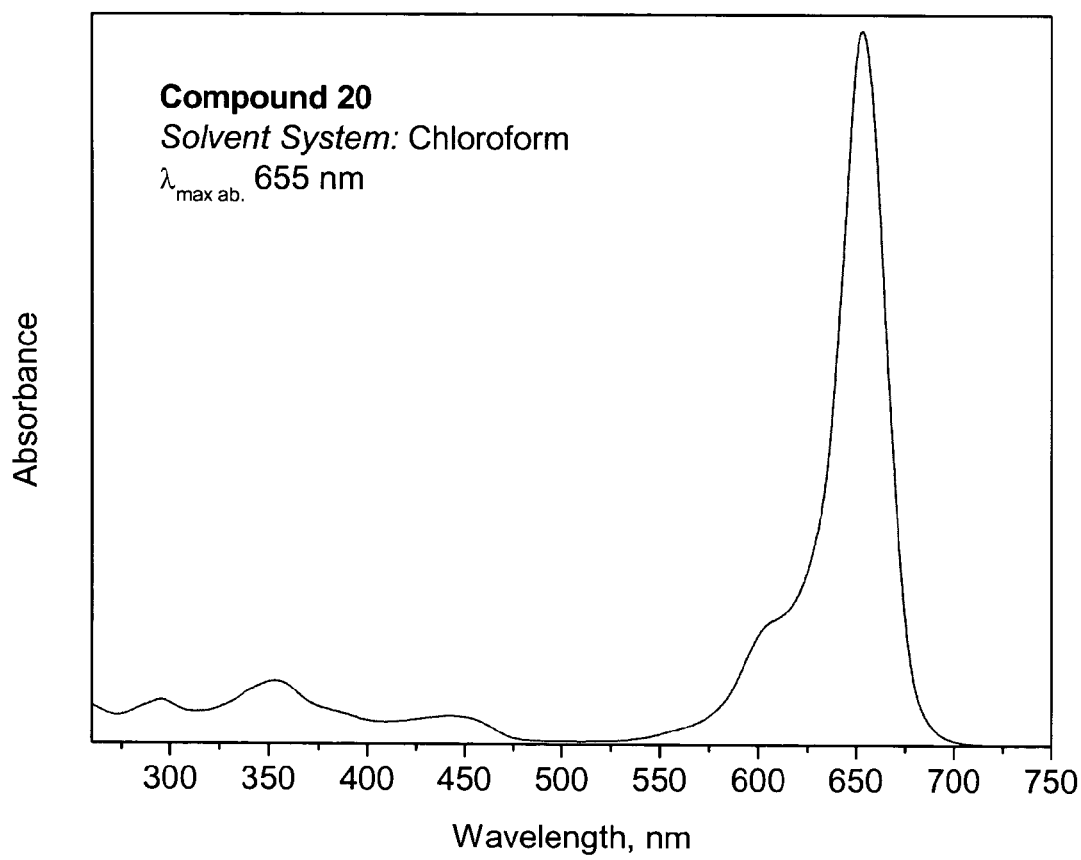
FIG. 4 is a plot of the absorption spectrum of compound 20 in chloroform.

Such positive effects have been already observed and are described in U.S. Patent Application Publication No. 2002/0077487 A1, which is hereby incorporated by reference. The introduction of additional spacer groups in 3-position of cationic cyanine dyes (FIG. 2, A) and an increase in the number of sulfonic groups gave brighter dye-conjugates as compared to CY5 dye (FIG. 2, B). As shown in FIG. 3 the ALEXA dye-conjugates are as much as 3 times brighter, when compared to CY5 dye-conjugates at higher dye-protein ratios. A similar increase in the total luminescence intensity (brightness) is also expected for the squaraine dyes shown in Examples 12–14.

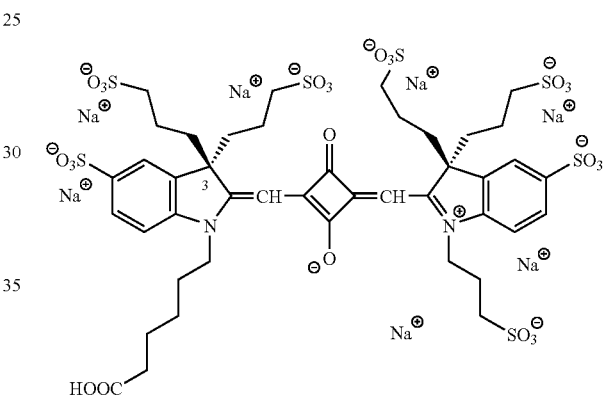

The synthesis of the symmetrial compound 24 is analogous to that described in Example 2 below, and by U.S. Pat. No. 6,538,129 B1, which is hereby incorporated by reference, using 2 equivalents of the indolenine 1d and squaric acid (2a).

The asymmetric compound 26 may also be synthesized similar to the procedure given in U.S. Pat. No. 6,538,129 B1 (see Example 3 below) or as described in PCT Patent Application Ser. No. PCT/US03/10995, filed Apr. 10, 2003. The use of BuOH/Toluene as the solvent sometimes converts the carboxyl substituent into a butyl ester. Example 2 describes the conversion of this ester into a free acid.

EXAMPLE 1

Synthesis of Precursors

This section describes the synthesis of various precursors. p-hydrazinobenzenesulfonic acid (Illy et al., J. Org. Chem. 33, 4283–4285 1968), 1-(5-carboxypentyl)-2,3,3-trimethyl-3H-5-indoliumsulfonate (1a), 2,3,3-trimethylindole-5-sulfonic acid potassium salt (1b), 1-(4-sulfonato propyl)-2,3,3-trimethylindoleninium-5-sulfonate (1h) (Mujumdar et al., Bioconj. Chem. 4(2) 105–111, 1993), and 1,2,3,3-tetramethylindoleninium-5-sulfonate (1c) were synthesized using literature procedures. 1d–1f are synthesized according to the procedures provided in U.S. Patent Application Publication No. 2002/0077487. 1-(2-phosphonethyl)-2,3,3-trimethylindoleninium-5-sulfonate (1i) is described in PCT Patent Application Publication No. WO 01/36973. 1,3-Dithiosquaric acid disodium salt (2c) and triethylammonium 2-butoxy-3-dicyanomethylene-4-oxo-1-cyclobuten-1-olate (2d) were synthesized according to Seitz et al., Chem. Ber. 112, 990–999, (1979) and Gerecht et al., Chem. Ber. 117, 2714–2729 (1984), respectively.

The 3-cyanoimino-4-oxo-1-cyclobutene-1,2-diolate (2e) is synthesized starting from dibutylsquarate according to the procedure of K. Köhler et al. Chem. Ber. 118, 1903–1916 (1985).

Synthesis of 1-(5-carboxypentyl)-2,3,3-trimethyl-3H-5-indoliumsulfonate (1a)

p-Hydrazinobenzenesulfonic acid 33 g of sodium carbonate was added to a suspension of 104 g (0.6 mol) of p-aminobenzenesulfonic acid in 400 mL of hot water. The solution was cooled to 5° C. in an ice-bath, and 70 g of concentrated sulfuric acid were added slowly under rapid stirring. A solution of 42 g of sodium nitrite in 100 mL of water was then added under cooling. A light yellow diazo-compound precipitate formed, which was filtered and washed with water, but not dried.

The wet diazo-compound was added under stirring and cooling (5° C.) to a solution of 170 g of sodium sulfite in 500 mL of water. The solution, which turned orange, was stirred under cooling for 1 h, and then heated to reflux. Finally, 400 mL of concentrated hydrochloric acid were added. The solution turned yellow, and the product precipitated as a white solid. For complete decoloration, 1–2 g of powdered zinc were added. The reaction mixture was cooled overnight, and the precipitate was filtered, washed with water, and dried in an oven at 100° C.

Yield: 96 g (85%), white powder; M.P.=286° C. (Lit. = 285° C.); $R_f$: 0.95 (RP-18, water:MeOH 2:1).

Preparation of 2,3,3-trimethylindole-5-sulfonic acid, potassium salt (1b)

18.2 g (0.12 mol) of p-hydrazinobenzenesulfonic acid and 14.8 g (0.17 mol) of isopropylmethylketone were stirred in 100 mL of glacial acetic acid at room temperature for 1 h. The mixture was then refluxed for 4 h. The mixture was cooled to room temperature, and the resulting pink solid precipitate was filtered and washed with ether.

The precipitate was dissolved in methanol, and a concentrated solution of potassium hydroxide in 2-propanol was added until a yellow solid completely precipitated. The precipitate was filtered, washed with ether, and dried in a desiccator over $P_2O_5$.

Yield: 20.4 g (71%), off-white powder; M.P.=275° C.; $R_f$: 0.40 (silica gel, isopropanol:water:ammonia 9:0.5:1).

1-(5-carboxypentyl)-2,3,3-trimethyl-3H-5-indoliumsulfonate (1a)

15.9 g (57 mmol) of 2,3,3-trimethylindolenium-5-sulfonic acid potassium salt and 12.9 g (66 mmol) of 6-bromohexanoic acid were refluxed in 100 mL of 1,2-dichlorobenzene for 15 min under a nitrogen atmosphere. The solution was cooled to room temperature, and the resulting pink precipitate was filtered, washed with chloroform, and dried.

Yield: 15.8 (58%), pink powder; $R_f$: 0.75 (RP-18, MeOH:water 2:1).

Synthesis of 1,2,3,3-tetramethylindolium-5-sulfonate (1c)

1.1 g of 2,3,3-trimethylindoleninium-5-sulfonate were suspended in 30 mL of methyl iodide. The reaction mixture was heated to boiling for 25 h in a sealed tube. After the mixture was cooled, excess methyl iodide was decanted, and the residue was suspended in 50 mL of acetone. The solution was filtered, and the residue was dried in a desiccator over $CaCl_2$. The resulting light yellow powder was used without further purification.

Yield: 90%, light yellow powder.

Synthesis of 3-(5-carboxypentyl)-2,3-dimethyl-5-sulfo-1-(3-sulfopropyl) indolium sodium salt (1d), (Scheme I)

A mixture of 25 g of ethyl 2-methylacetoacetate (I), 64 ml of 21% sodium ethoxide solution in ethanol and 34 mL of ethyl-6-bromohexanoate is refluxed in 200 mL of ethanol overnight. The mixture is filtered and the solvent is removed under reduced pressure. The residue is partitioned between 1 M HCl and chloroform.

The organic layer is dried over magnesium sulfate and purified on silica gel using 1:10 ethyl acetate/hexane as the eluent to yield 22 g of ethyl 2-(5-carboethoxypentyl)-2-methylactoacetate (IIa)

The above compound is dissolved in 300 ml of methanol. A solution of 10 g NaOH in 100 mL water is added. The mixture is heated at 50° C. overnight. The solution is reduced to about 50 mL, acidified to pH 1 and extracted with ethyl acetate. The organic phase is collected, dried over $MgSO_4$ and evaporated to yield 13.5 g of 7-methyl-8-oxononanonic acid (IIIa).

The nonanonic acid is refluxed in 110 mL of acetic acid with 13.5 g of 4-hydrazinobenzenesulfonic acid for 4 hours. The acetic acid is evaporated and the product is purified on silica gel to yield 23 g of the product (IVa).

To the methanol solution of 11 g of Compound IVa is added 3.4 g of anhydrous sodium acetate. The mixture is stirred for five minutes. The solvent is evaporated and the resulting sodium salt is heated with 24.4 g of propane sultone at 110° C. for 1 hour to generate the final product 1d.

Synthesis of 3-(6-hydroxyhexyl)-2,3-dimethyl-5-sulfo-1-(3-sulfopropyl) indolium, sodium salt (1e)

Another starting material 1e is synthesized analogously using ethyl 2-methylacetoacetate and 6-benzoyl-1-bromohexane in the presence of 1.2 equivalents of sodium hydride in THF according to 1d. After isolating the 3-(6-hydroxyhexyl)-2,3-dimethyl-5-sulfo-indolium, inner salt (the hydroxy group is again protected and the compound is quarternized using propanesultone. Deprotection is achieved using dilute NaOH.

1f is synthesized analogously taking into account the more polar nature of the sulfonic groups that are introduced either by reaction with 2-bromo-ethane-sulfonic acid, propane- or butanesultone. Sulfogroups can also be introduced by reaction of a 3-carboxy-alkyl-substituted compound like 1d with taurine according to Terpetschnig et al. Anal. Biochem. 217, 197–204 (1994).

Using 4-hydrazino-benzoic acid as described in Anal. Biochem. 217, 197–204 (1994) or 4-hydrazino-phenyl-acetic acid as described in Cytometry 11(3), 418–30 (1990) and reacting them in a Fisher indole synthesis With 7-methyl-8-oxononanonic acid or one of the other functionalized precursors as described above, 5-carboxy-derivatized indoles such as 1g that contain a spacer group in position 3 can be synthesized.

Other compounds that contain functional groups in both $R_3$ and $R_4$ can be synthesized accordingly and used as starting materials for squaraine dyes of this invention. $R_3$ and $R_4$ can also be a part of an aliphatic ring system as described in U.S. Patent Application Publication No. 2002/0017487.

Selected precursor compounds are shown below
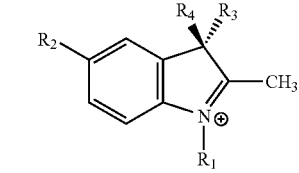
| 1 | $R_1$ | $R_2$ | $R_3$ (x = 2, 3, 4) | $R_4$ |
|---|---|---|---|---|
| a | $(CH_2)_5COOH$ | $SO_3^-$ | $CH_3$ | $CH_3$ |
| b | — | $SO_3K$ | $CH_3$ | $CH_3$ |
| c | $CH_3$ | $SO_3^-$ | $CH_3$ | $CH_3$ |
-continued
| 1 | $R_1$ | $R_2$ | $R_3$ (x = 2, 3, 4) | $R_4$ |
|---|---|---|---|---|
| d | $(CH_2)_3SO_3Na$ | $SO_3^-$ | $(CH_2)_5COOH$ | $CH_3$ |
| e | $(CH_2)_3SO_3Na$ | $SO_3^-$ | $(CH_2)_6OH$ | $CH_3$ |
| f | $(CH_2)_3SO_3Na$ | $SO_3^-$ | $(CH_2)_xSO_3Na$ | $CH_3$ |
| g | $(CH_2)_3SO_3^-$ | $COOH$ | $(CH_2)_5COOH$ | $CH_3$ |
| h | $(CH_2)_3SO_3Na$ | $SO_3^-$ | $CH_3$ | $CH_3$ |
| i | $(CH_2)_2PO(OH)_2$ | $SO_3^-$ | $CH_3$ | $CH_3$ |
Scheme I
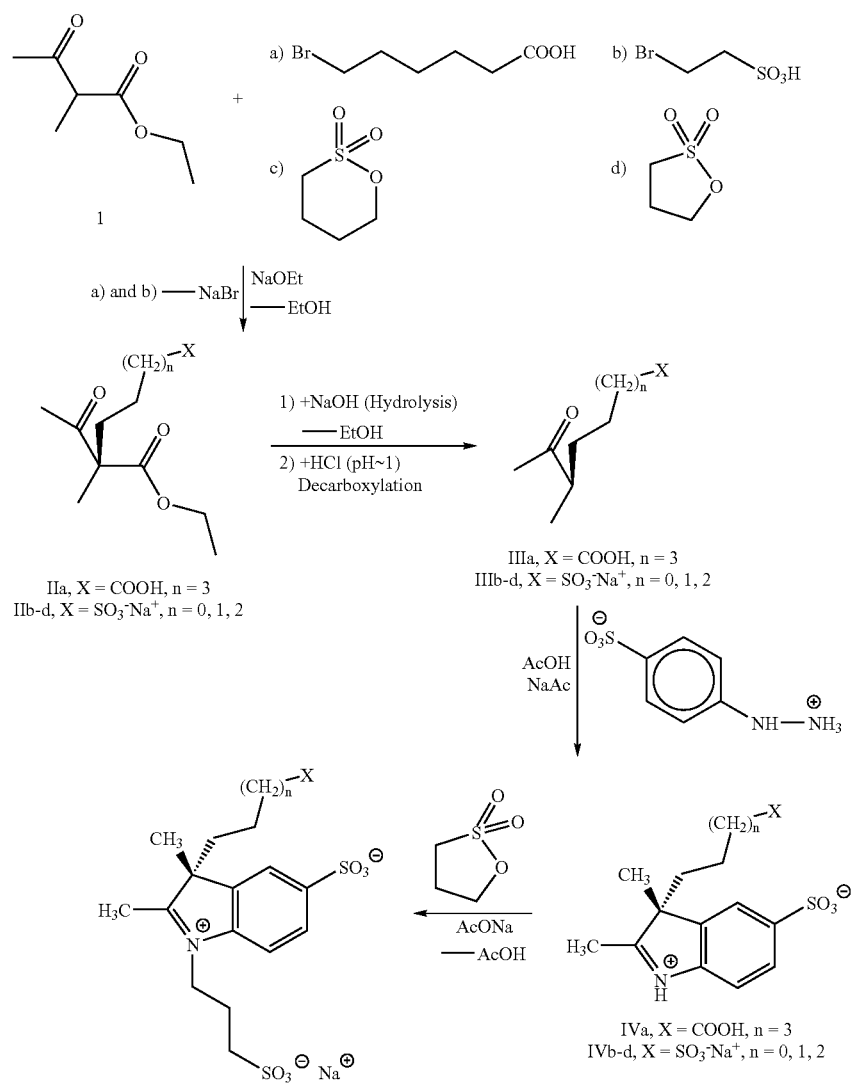

|   | $R_1$ | $R_2$ | $R_3$ | $R_4$ |
|---|---|---|---|---|
| a | O | O | OH | OH |
| b | O | O | $OC_4H_9$ | $OC_4H_9$ |
| c | S | O | $S^- Na^+$ | $O^- Na^+$ |
| d | O | $C(CN)_2$ | $OC_4H_9$ | $O^- HNEt_3^+$ |
| e | N—CN | O | $O^- K^+$ | $O^- K^+$ |

EXAMPLE 2

Synthesis of 2,4-bis[N-(carboxypentyl)-3,3-dimethyl-5-sulfo-2-indolinylidene methyl]cyclobutenediylium-1,3-diolate NHS ester (4)

Synthesis of the di-butylester (3a)

120 mg (1.03 mmol) of squaric acid (2a) were added to 1 g (2.17 mmol) of 1-(5-carboxypentyl)-2,3,3-trimethyl-3H-5-indoliumsulfonate (1a). The resulting mixture was refluxed in 50 mL of 1-butanol:toluene (1:1, v:v) for 22 h using a Dean-Stark trap filled with 4A molecular sieve. After the mixture was cooled, the solvent was removed, and the product was purified by preparative thin-layer chromatography using RP-18 glass plates and methanol:water (2:1, v:v) as eluent to give 3a.

Yield: 90 mg (22%) of 3a; M.P.>300° C.; $R_f$: 0.47 (RP-C18, methanol/water2/1); FAB-MS, m/e (M$^+$, dianion) for $C_{46}H_{58}N_2O_{12}S_2K_2$, calculated 895.1, found 894.8; $^1$H-NMR (D$_2$O): δ 7.7–7.1 (m, 6H), 5.7 (s, 2H), 3.7 (t, 4H, J=6.5), 2.0 (t, 4H, J=7 Hz), 1.55–0.9 (m, 24H), 1.45 (s, 12H), 0.5 (t, 6H, J=7 Hz; $\lambda_{max}$ (abs)=634 nm (PBS), $\lambda_{max}$ (em)= 642 nm (PBS).

Synthesis of di-acid (3b)

1 mL of water and 20 mL of 1 M HCl were added to 50 mg (0.05 mmol) of Sq635-b-butylester (3a). The resulting mixture was heated to 100° C. for 80 min. At the end of the reaction, 5 mL of 1 M HCl were added. After the mixture was cooled, the solvent was removed, and the product was vacuum dried. The product was used without further purification Yield: 43 mg (99%); M.P.>300° C.; $R_f$: 0.75 (RP-C18, methanol:water 2:1); FAB-MS, m/e (M$^+$, dianion) for $C_{38}H_{42}N_2O_{12}S_2K_2$, calculated 782.9, found 783.0; $^1$H-NMR (D$_2$O): δ 7.8–7.3 (m, 6H), 5.9 (s, 2H), 4.2 (t, 4H, J=6.5 Hz), 2.4 (t, 4H, J=7 Hz), 1.95–1.3 (m, 12H), 1.77 (s, 12H); $\lambda_{max}$(abs)=635 nm (PBS); $\lambda_{max}$(em)=642 nm (PBS).

| Squaraine | R |
|---|---|
| 3a | $C_4H_9$ |
| 3b | H |
| 4 | NHS |

Synthesis of bis-NHS-ester (4)

a) With TSTU (N,N,N',N'-tetramethyl(succinimido)uronium tetrafluoroborate)

26 μl (0.15 mmol) of diisopropylethylamine and 38 mg (0.126 mmol) of TSTU were added to a mixture of 43 mg (0.05 mmol) of Sq635-b-acid (3b) in 1 mL of DMF, 1 mL of dioxane, and 0.5 mL of water. After 30 min, the mixture was filtered, and the solvents were removed in vacuum. The product was dried over $P_2O_5$ and used without further purification.

Yield: 40 mg (76%); M.P.>300° C.; $R_f$: 0.82 (RP-C18, methanol:water 2:1); FAB-MS, m/e (M$^+$, dianion) for $C_{46}H_{48}N_4O_{16}S_2K_2$, calculated 977.0, found 977.1; ε=140,000 L/(mol*cm).

b) With NHS/DCC 1 mL of anhydrous DMF was added to a mixture of 20 mg (0.023 mmol) of Sq635-b-acid (3b), 14 mg (0.069 mmol) of dicyclohexylcarbodiimide (DCC), and 8 mg (0.069 mmol) of N-hydroxysuccinimide (NHS). The solution was stirred for 24 h at room temperature and then filtered. The solvent was removed in vacuum, and the product was triturated with ether and dried over $P_2O_5$.

Yield: 22 mg (91%); M.P.>300° C.; $R_f$: 0.82 (RP-C18, methanol:water 2:1); FAB-MS, m/e ($M^+$, dianion) for $C_{46}H_{48}N_4O_{16}S_2K_2$, calculated 977.0, found 977.2.

EXAMPLE 3

Synthesis of 2-[N-(5-carboxypentyl)-3,3-dimethyl-5-sulfo-2-indolinylidene methyl]-4-[3,3-dimethyl-5-sulfo-2-indolinylidenemethyl]cyclobutenediylium -1,3-diolate (6a)

Synthesis of mono-acid (6a)

22 µl (0.1 mmol) of squaric acid dibutyl ester were added to 47 mg (0.1 mmol) of 1-(5-carboxypentyl)-2,3,3-trimethyl-3H-5-indoliumsulfonate (1a). The resulting mixture was refluxed in 8 mL of ethanol with 140 µL of triethylamine for 30 min. 220 µl of 1 M aqueous NaOH were then added, and the mixture was refluxed for 30 min. After the mixture was cooled to room temperature, 2.3 mL of 1 M hydrochloric acid were added, and the solvent was removed under reduced pressure to obtain the monosubstituted squaraine derivative (5a).

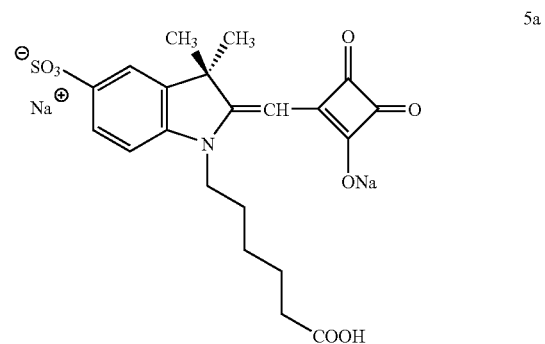

5a

The residue was refluxed with 24 mg (0.09 mmol) of 2,3,3-trimethylindole-5-sulfonic acid (1b) potassium salt in butanol:toluene (1:1 v:v) for 1 h. Water was removed as an azeotrope using a Dean-Stark trap. After cooling, the solvents were removed using a rotary evaporator. The product was treated with 100 µL of methanol, collected under reduced pressure, and purified on preparative TLC (RP-18 $F_{254S}$) using methanol:water (2:1 v:v) as the eluent.

Yield: 31 mg (33%); M.P.>300° C.; $R_f$: 0.50 (RP-C18, methanol:water 2:1); FAB-MS, m/e ($M^+$, dianion) for $C_{32}H_{32}N_2O_{10}S_2K_2$, calculated 668.1, found 668.5; $^1$H-NMR ($D_2O$): δ 7.75–7.5 (m, 4H), 7.15–6.95 (m, 2H), 5.55 (s, 1H), 5.35 (s, 1H), 4.55 (t, 2H, J=6.5 Hz), 2.05–2.3 (m, 2H), 1.5–1.2 (m, 6H), 1.25 (t, 12H).

Synthesis of NHS-ester (6b)

The activation of (6a) to the NHS-ester (6b) was carried out in analogy with the activation of the bis-acid (3b) procedure (b), using one equivalent of NHS and 1,2 equivalents of DCC.

Analysis: M.P.>300° C.; $R_f$: 0.55 (RP-C18, methanol:water 2:1); FAB-MS, m/e ($M^+$, dianion) for $C_{36}H_{35}N_3O_{12}S_2K_2$, calculated 766.1, found 766.4; $^1$H-NMR ($D_2O$): δ 7.85–7.5 (m, 4H), 7.15–6.9 (m, 2H), 5.55 (s, 1H), 5.35 (s, 1H), 4.45 (t, 2H, J=6.5 Hz), 2.7 (s, 4H) 2.05–2.35 (m, 2H), 1.5–1.2 (m, 6H), 1.25 (t, 12H).

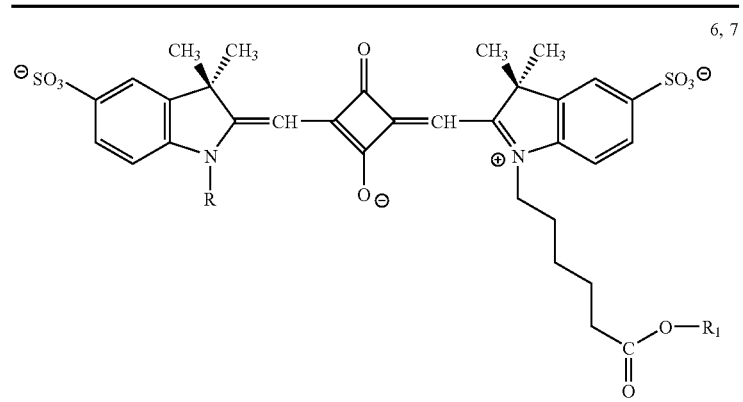

6, 7

| Squaraine | R | R |
|---|---|---|
| 6a | H | H |
| 6b | H | NHS |
| 7a | $CH_3$ | H |
| 7b | $CH_3$ | NHS |

EXAMPLE 4

Synthesis of 2-[N-(5-carboxypentyl)-3,3-dimethyl-5-sulfo-2-indolinylidene methyl]-4-[1,3,3-trimethyl-5-sulfo-2-indolinylidenemethyl]-cyclobutene diylium-1,3-diolate (7a)

Synthesis of mono-acid (7a)

1 g (2.4 mmol) of 1,2,3,3-tetramethylindolium-5-sulfonate (1c) was dissolved in 10 mL of ethanol containing 50 μL of triethylamine. The temperature of the reaction mixture was increased to 40° C., and 640 μl (2.9 mmol) of squaric acid dibutyl ester (2c) were slowly added. The reaction mixture was then heated to 60° C. and stirred for 4 h. After the mixture was cooled to room temperature, the solvent was removed under reduced pressure, and the yellow crystalline residue was used without further purification.

In the next step, 860 mg of 1-(ε-carboxypentyl)-2,3,3-trimethylindolenium-5-sulfonate (1a) in a butanol/toluene mixture (1/1 v:v) were added and refluxed for 5 h using a Dean-Stark trap. After the mixture was cooled, the solvents were removed under reduced pressure. The product was purified on preparative TLC (RP-18 $F_{254S}$) using methanol:water (2:1 v:v) as the eluent. 150 mg of the raw product were dissolved in 1 mL methanol and separated on a preparative TLC plate.

Yield: 50 mg (30%); M.P.>300° C.; $R_f$: 0.75 (RP-C18, methanol/water 2/1); FAB-MS m/e calculated for $C_{33}H_{34}N_2O_{10}S_2K_2$ ($M^{2-}$) 682.8, found 683.0; $^1$H-NMR ($D_2O$): δ 7.70–7.55 (m, 4H), 7.20–7.00 (m, 2H), 5.50 (s, 1H), 5.40 (s, 1H), 4.45 (t, 2H, J=6.5 Hz), 4.00 (s, 3H), 2.05–2.30 (m, 2H), 1.50–1.25 (m, 6H), 1.20 (t, 12H); analysis: calculated for $C_{33}H_{34}N_2O_{10}S_2K_2$*$2H_2O$: C 49.73; H 4.81; N 3.52. found: C 49.60; H 4.74; N 3.58.

Synthesis of NHS-ester (7b)

The activation of (7a) to the NHS-ester (7b) was carried out in analogy with the activation of the bis-acid (3b) procedure b), using one equivalent of NHS and 1,2 equivalents of DCC.

EXAMPLE 5

Synthesis of 2,4-Bis[1,3,3-trimethyl-2-indolinylidenemethyl]cyclobutene diylium-1,3-dithiolate (9)

2,4-Bis[1,3,3-trimethyl-2-indolinylidenemethyl]cyclobutenediylium -1,3-dioxolate (8)

Squaraine dye (8) was synthesized according to Terpetschnig et al. (1993).

Analysis: $^1$H-NMR (CDCl$_3$, TMS): δ 1.78 (s, 12H), 3.57 (s, 6H), 5.92 (s, 2H), 7.01(d, 2H), 7.16 (t, 2H), 7.28 (d, 2H), 7.35 (t, 2H); $λ_{max}$(abs)=633 nm (CHCl$_3$); $λ_{max}$(em)=653 nm (CHCl$_3$); ε=307,000 (CHCl$_3$) L/(mol*cm).

Dithio-squaraine (9)

0.32 g (0.75 mmol) of squaraine dye (8) and 0.40 g (0.90 mmol) of phosphorus pentasulfide $P_2S_5$ were refluxed in 6.5 mL of pyridine with stirring for 5 h. After cooling, the resulting precipitate was filtered, and washed with 3 mL of pyridine and 30 mL of ether. The precipitate was purified by column chromatography on Silcagel C-120 using chloroform as a solvent, and was recrystallized from pyridine.

Yield: 0.18 g (53%), before purification; M.P.=271° C.; sulfur analysis for $C_{28}H_{28}N_2S_2$, S (cal): 14.04%, S (found): 13.53%; $^1$H-NMR (CDCl$_3$, TMS): δ 1.75 (s, 12H), 3.83 (s, 6H), 6.21, (s, 2H), 7.09 (d, 2H), 7.21 (t, 2H),7.27 (d, 2H), 7.36 (t, 2H); $λ_{max}$(abs)=658 nm (CHCl$_3$), $λ_{max}$(em)=707 nm (CHCl$_3$); ε=150,000 (CHCl$_3$) L/(mol*cm).

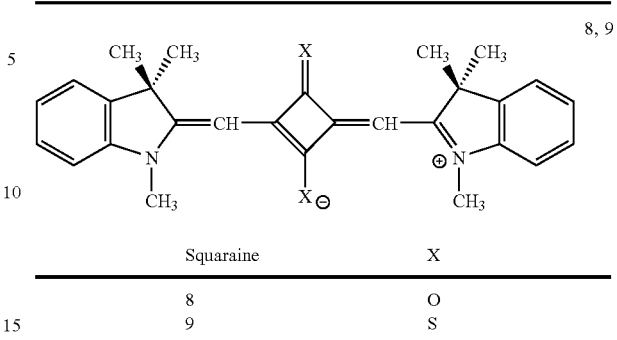

| Squaraine | X |
|---|---|
| 8 | O |
| 9 | S |

Synthesis of 2-[3,3-dimethyl-2-1(H)indolinylidenemethyl]4-[1-ethyl-benzoselanzolinylidene-methyl]cyclobutenediylium-1,3-dithiolate (11)

2-[3,3-dimethyl-2-1(H)indolinylidenemethyl]4-[1-ethyl-benzoselenazolinylidene-ethyl]cyclobutenediylium-1,3-dioxolate (10c)

Synthesized according to Terpetschnig et al., Dyes & Pig. 21, 227,1993)).

1-[3'-Ethyl-2(3H)benzoselenazolylidene-2-methyl]3-ethoxycyclobuten-3,4-dione (10a)

15 mmol of N-ethyl-2-methylbenzoselenazolium iodide were added to a stirred hot solution of 10 mmol ethylsquarate and 2 mL triethylamine in 15 mL of ethanol. The solution was kept at 70–80° C. for 5 min, and then cooled to room temperature. The resulting yellow-to-red colored precipitate was isolated, washed with ethylether, and dried. The product was purified by column chromatography on silica gel using CHCl$_3$:EtOAc (9:1, v:v) as eluent.

Yield: 58%; M.P.=278–80° C.; $^1$H-NMR (D$_6$-DMSO): δ 1.40 (t, 3H), 1.52 (t, 3H), 4.07 (q, 2H), 4.84 (q, 2H), 5.69 (s, 1H), 7.05 (d, 1H), 7.13 (t, 1H), 7.35 (t, 1H), 7.55 (d, 1H).

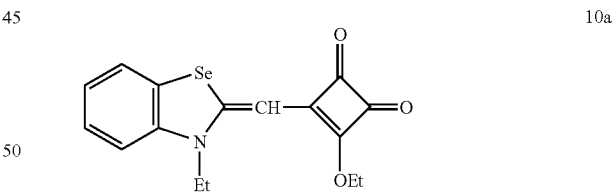

2-Hydroxy-1-[3'-ethyl-2(3H)benzoselanzolylidene-2'-methyl]cyclobuten-3,4-dione (10b)

5 mmol of (10a) were suspended in 20 mL of boiling ethanol, and dissolved on addition of 0.6 mL of 40% NaOH. The solution was kept at boiling for another 5 min and then cooled to room temperature. After addition of 6–7 mL of 2 M HCl, the ethanol solution was concentrated, and the resulting precipitate was collected and used without further purification.

Yield: 95%; M.P.=252–254° C.; $^1$H-NMR(D$_6$-DMSO): δ 1.24 (t, 3H), 4.07 (q, 2H), 4.1 (q, 2H), 6.08 (s, 1H), 7.09 (t, 1H), 7.32 (m, 2H), 7.81 (d, 1H).

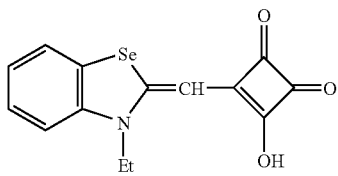

Squaraine (11 a or 11 b)

1 mmol of the squaric acid derivative (10b) and 1 mmol of 2-methylene-1,3,3-trimethylindolenine or 2-methylene-3,3-dimethylindolenine (from Aldrich) were heated under reflux in a mixture of 20 mL toluene and 20 mL 1-butalnol. Water was removed azeotropically using a Dean-Stark trap. After 16 h, the reaction was cooled to room temperature, and the solvents were removed under vacuum. The residue was treated with either, and the product was isolated by filtration. Further purification was achieved using column chromatography with chloroform-2-propanol mixtures as eluent.

Yield: 88% of (11a); M.P.=278–280 °C.; $^1$H-NMR (CDCl$_3$): δ 1.45 (t, 3H), 1.77 (s, 6H), 3.46 (s, 3H), 4.23(q, 2H), 5.76 (s, 1H), 6.19 (s, 1H), 6.94(d, 1H), 7.09 (t, 1H), 7.31 (t, 1H), 7.32(d, 1H), 7.39 (d, 1H) 7.41 (t, 1H), 7.62 (d, 1H); $\lambda_{max}$(abs)=657 nm (CHCl$_3$); $\lambda_{max}$(em)=675 nm (CHCl$_3$).

Yield: 80% of (11b); $^1$H-NMR(CDCl$_3$): δ 1.5 (s, 9H), 4.25 (m, 2H), 5.45 (s, 2H), 7.65–7.15 (m, 8H), 12.2 (s, 1H).

Thiosquaraine (12a) and (12b)

40 mg (0.087 mmol) of 2-hydroxy-1-[3'-ethyl-2(3H)benzoselanzolylidene-2'-methyl]cyclobuten-3,4-dione (11a) and 70 mg (0.144 mmol) of P$_2$S$_5$ were refluxed for 5 h in 2 mL of pyridine under stirring. The solvent was removed under reduced pressure, and the residue was treated with chloroform. Chloroform was removed under reduced pressure, and the product was purified using preparative TLC, again using chloroform as the solvent system.

Analysis: $\lambda_{max}$(abs)=687 nm (CHCl$_3$); $\lambda_{max}$(em)=724 nm (CHCl$_3$).

In an analogous procedure, -20 mg of squaraine (11b) and 30 mg of phosphor pentasulfide P$_2$S$_5$ were reacted in 1.5 mL of pyridine for 4 h. The compound (12b) was purified as described above.

Analysis: $\lambda_{max}$(abs)=690 nm (CHCl$_3$); $\lambda_{max}$(em)=724 nm (CHCl$_3$).

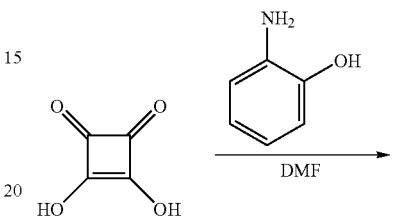

| Squaraine | R | X |
|---|---|---|
| 11a | CH$_3$ | O |
| 11b | H | O |
| 12a | CH$_3$ | S |
| 12b | H | S |

EXAMPLE 6

Synthesis of 2,4-Bis[N-(5-carboxypentyl)-3,3-dimethyl-5-sulfo-2-indolinylidene methyl]cyclobutenediylium-1,3-dithiolate (13)

1,3-Dithiosquaric acid disodium salt (2c)

2-(2-Hydroxyanillino)-4-[1-(2-hydroxyphenyl)ammonio]-3-oxo-1-cyclobutene-1-olate A solution of 20 mL of DMF, 4 g (35 mmol) of squaric acid, and 7.2 g (66 mmol) of o-aminophenole was refluxed for 1.5 h using a mechanical stirrer. The yellow precipitate was filtered off, washed with ether, and dried in a desiccator over CaCl$_2$. The product was used without further purification.

Yield: 4.7 g (80%), yellow powder.

1,3-Thiosquaric acid, disodium salt (2c)

3.52 g (21 mmol) of 2-(2-Hydroxyanilino)-4-[1-(2-hydroxyphenyl) ammonio]-3-oxo-1-cyclobutene-1-olate and H, m); $\lambda_{max}$(abs)=642 nm (HSA-conjugate in PBS); $\lambda_{max}$ (em)=654 nm (HSA-conjugate in PBS).

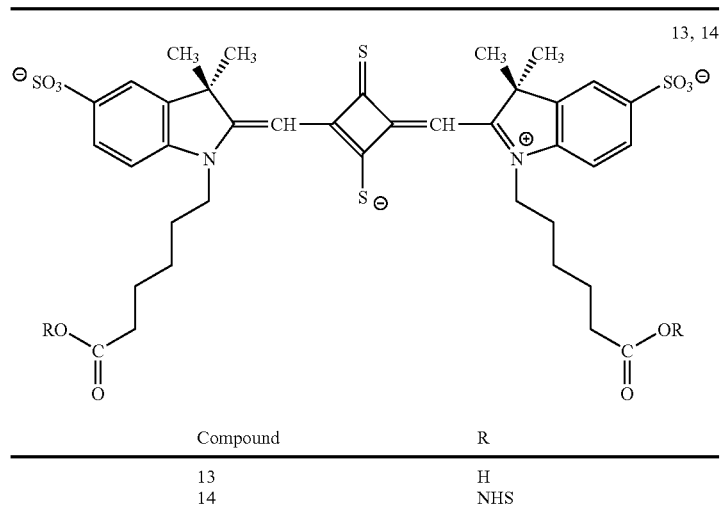

| Compound | R |
|---|---|
| 13 | H |
| 14 | NHS |

1.30 g (35 mmol) of sodium hydrogenesulfide monohydrate were refluxed for 30 min in 50 mL of dry ethanol. An orange precipitate was formed, which was filtered off and washed with ethanol, acetonitrile, and ether. The product was dried in a desiccator over $CaCl_2$.

Yield: 2.4 g (60%), orange powder.

Thio-squaraine,(13)

300 mg (0.64 mmol) of 1-(5-carboxypentyl)-2,3,3-trimethyl-3H-5-indoliumsulfonate (1a) and 62 mg (0.33 mmol) of 1,3-thiosquaric acid disodium salt (2c) were suspended in 16 mL of 1:1 butanol:toluene (v:v). The solution was heated to reflux for 4 h. The reaction was controlled by TLC (RP-C18, methanol:water 2:1, v:v), which showed a major spot at $R_f$: 0.75 for the diacid (13) and a minor spot at $R_f$: 0.55 for the dibutylester due to the esterification of the carboxylic acid groups in BuOH. After removal of toluene at reduced pressure, the reaction mixture was cooled to 4° C., and the precipitate was filtered. The crude product was redissolved in a mixture of 2.5 mL of methanol and 1 mL of water, and purified on an preparative RP-C18 plate using methanol:water (2:1, v:v) as eluent. The major band was collected, and the product was extracted using methanol as solvent.

Yield: 67 mg (9.6%); $R_f$: 0.75 (RP-C18, methanol:water 2:1); ESI-MS, m/e (M+, di-acid) for $C_{38}H_{42}N_2O_{10}S_4H_2$, calculated 816.9, found 817.5. $^1$H-NMR ($D_2O$): δ 8.00 (2H, s), 7.90 (2H, d), 7.80 (2H, d), 5.75 (1H, s), 4.35 (4H, t), 2.15 (4H, t), 1.85 (4H, m), 1.55 (4H, m), 1.50 (12H, s), 1.35 (4

Synthesis of bis-NHS-ester (14)

0.5 mL of anhydrous DMF was added to a mixture of 7.3 mg (0.009 mmol) of b-acid (13), 10.5 mg (0.05 mmol) of dicyclohexylcarbodiimide (DCC), and 2 mg (0.018 mmol) of N-hydroxysuccinimide (NHS). The solution was stirred for 24 h at room temperature and filtered. The solvent was removed in vacuum, and the product was triturated with ether and dried over $P_2O_5$.

Yield: 7 mg (91%); $R_f$: 0.82 (RP-C18, methanol/water 2/1).

EXAMPLE 7

Synthesis of 2,4-Bis[N-(ε-butoxycarbonylpentyl)-3,3-dimethyl-5-sulfo-2-indolinylidene methyl] cyclobutenediylium-3-dicyanomethylene-1-oxolate (15)

Triethylammonium 2-butoxy-3-dicyanomethylene-4-oxo-1-cyclobuten-1-olate (2d)

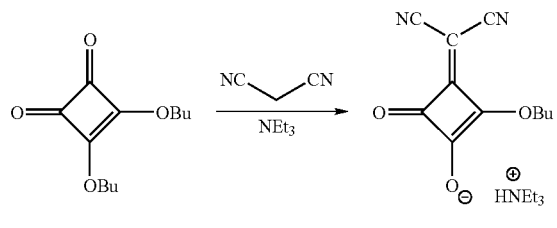

2d 2.16 ml (10 mmol) of 3,4-dibutoxy-3-cyclobutene-1,2-dione (2b) was dissolved in 20 ml of anhydrous benzene, and 660 mg (10 mmol) of malonodinitrile was added under stirring. Then, 1.65 ml (12 mmol) of triethylamine was added dropwise for 5 min followed by 10 ml of anhydrous benzene. The obtained emulsion is stirred for 30 min at room temperature. The solvent is removed using a rotary evaporator. The yellow oiled residue is treated three times with ether to give crude product 2d (1.8 g, 56%), $^1$H-NMR (DMSO-d$_6$): δ 10.15–9.55 (1H, broad s, NH$^+$), 4.59 (2H, t, 6.7 Hz, OCH$_2$), 3.07 (6H, q 7.4, 14.5 Hz, N(CH$_2$CH$_3$)$_3$), 1.77–1.58 (2H, m, CH$_2$), 1.48–1.26 (2H, m, CH$_2$), 1.18 (9H, t, 7.3 Hz, N(CH$_2$CH$_3$)$_3$), 0.90 (3H, t, 7.4 Hz, CH$_3$).

15

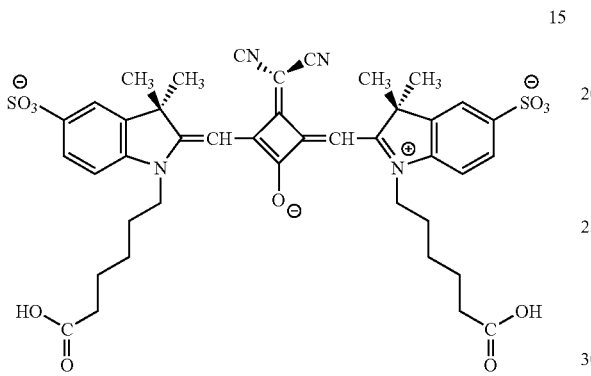

472 mg of 1-(5-carboxypentyl)-2,3,3-trimethyl-3H-5-indoliumsulfonate (1a) and 137 mg of triethylammonium 2-butoxy-3-dicyanomethylene-4-oxo-1-cyclobuten-1-olate (2d) were refluxed in 25 mL of butanol:toluene (1:1, v:v) for 4 h using a Dean-Stark trap. After the mixture was cooled to room temperature, the solvents were removed in vacuum, and the raw product was triturated with ether and dried. The raw product was purified by preparative thin-layer chromatography on RP-18 glass plates using a methanol/water mixture (2/1, v:v) as eluent. The blue-green band with an R$_f$ of 0.55 was collected.

Yield: 32%; FAB-MS m/e calculated for C$_{41}$H$_{44}$N$_4$O$_{11}$S$_2$K$_2$ (M$^{2-}$) 832.9, found 633.2. IR (KBr): 2100 cm$^{-1}$ (CN). $^1$H-NMR (D$_2$O): δ 8.00 (2H, s), 7.90 (2H, d), 7.75 (2H, d), —CH= is exchanged, 4.45 (4H, t), 2.10(4H, t), 1.85 (4H, m), 1.55 (4H, m), 1.45 (12H, s), 1.35 (4H, m); λ$_{max}$(abs)=667 nm (PBS), λ$_{max}$(em)=685 nm (PBS), (4%); λ$_{max}$(abs)=687 nm (PBS+HSA), λ$_{max}$(em)= 704 nm (PBS+HSA), (8%), ε=180.000 L/mol*cm (H$_2$O).

EXAMPLE 8

Synthesis of a reactive Croconium-dye (17)

Croconium dye (16)

0.8 g of 1-(δ-sulfonatobutyl)-2-methylbenzthiazolium iodide (as described in U.S. Pat. No. 3,793,313) and 0.15 g of croconic acid (Aldrich) were suspended in a mixture of 10 mL of pyridine and 0.3 mL of triethylamine. The mixture was stirred overnight at room temperature, the solvent was removed at reduced pressure, and the residue was triturated with methanol filtered and dried.

Yield: 0.6 g (50%).

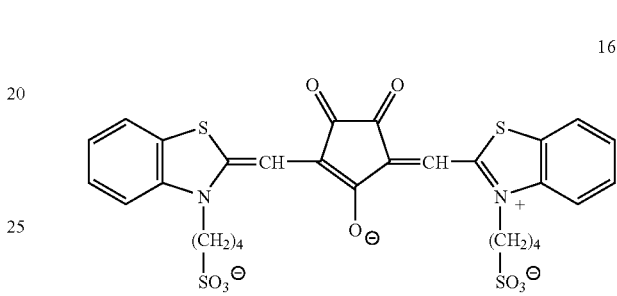

Synthesis of the sulfonyl chloride (17)

0.1 g of (16) and 0.3 g of PCl$_5$ were mixed in a mortar, and the mixture was heated in a round bottom flask for 30 min to 100 °C. 10 mL of toluene were then added, and the mixture was stirred for another 45 min at room temperature. The reaction mixture was transferred to a separation funnel, CHCl$_3$ was added, and the unreacted PCl$_5$ was removed by extraction with water. The organic layers were combined, and the solvents were removed under reduced pressure. The product was dried under vacuum.

Yield: 0.05 g.

EXAMPLE 9

Synthesis of intermediates for asymmetrical squaraines

The syntheses of these intermediates are described in A. L. Tatarets et al., Dyes & Pig. (in press), Terpetschnig et al., Dyes & Pig. 21, 227,1993 and in PCT application PCT/US03/10995 filed Apr. 10, 2003. The mono-substituted squaraine 18 is reacted with one equivalent of the CH-acidic compound (e.g. barbituric acid, 2-nitro-ethylacetate and other similar compounds) in EtOH in presence of triethylamine to yield squaraine-ring substituted derivatives:

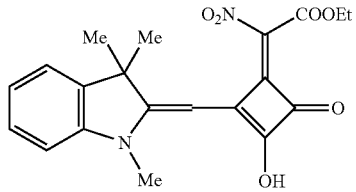

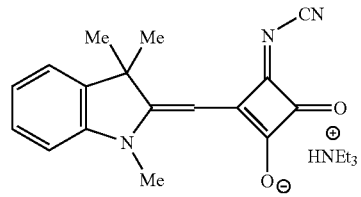

-continued

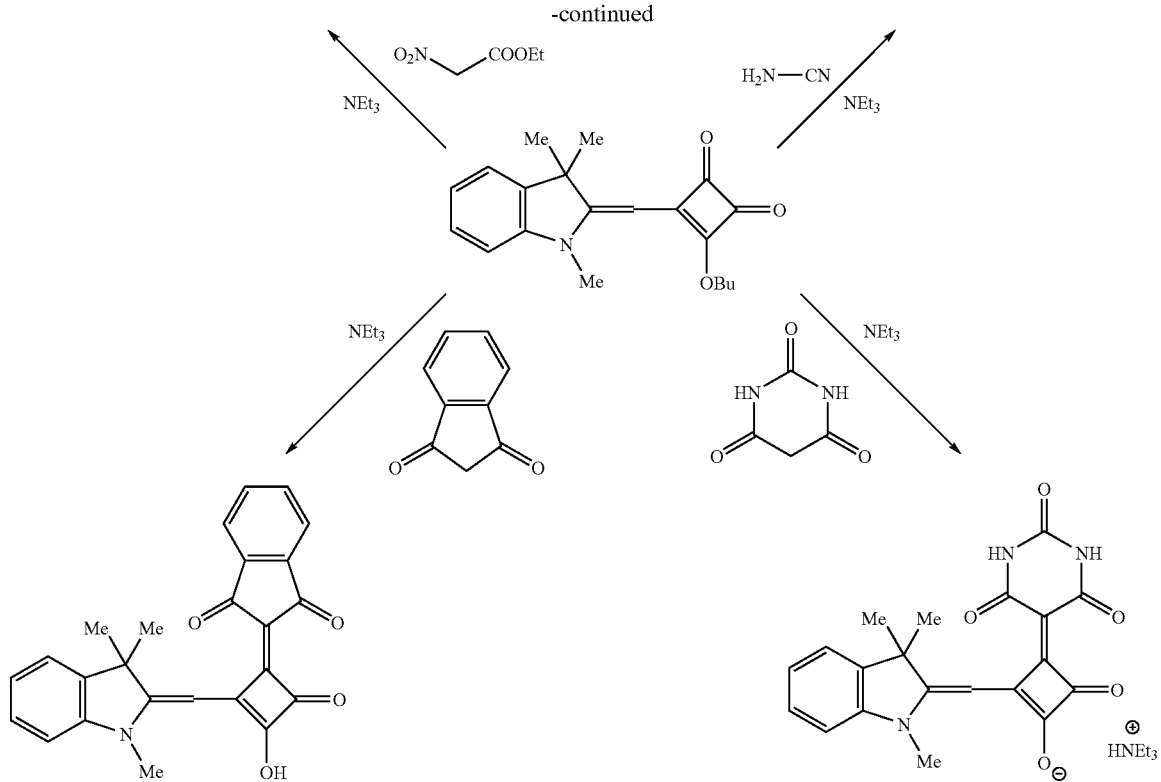

EXAMPLE 10

Synthesis of Cyanimino-squaraine dyes (20)-(22)

a) Synthesis of dye 20

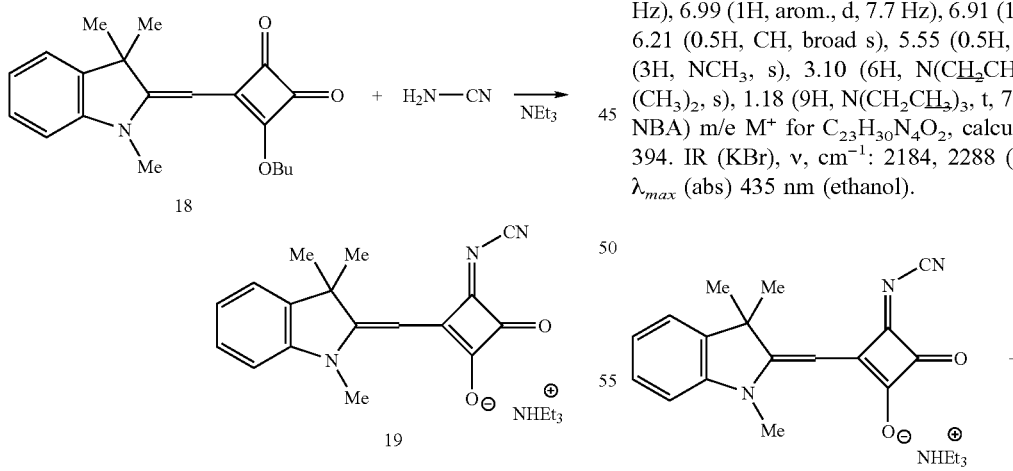

A mixture of 1 g (3.1 mmol) of 3-butoxy-4-(1,3,3-trimethyl-2,3-dihydro-1H-2-indolylidenmethyl)-3-cyclobutene-1,2-dione (18), 200 mg (4.8 mmol) of cyanamide and 0.5 ml (3.6 mmol) of triethylamine is refluxed with stirring in 10 ml of absolute ethanol for 12 h. The solvent is removed under reduced pressure by a rotary evaporator. The obtained gum is column purified (Silica gel 60, 0–5% methanol-chloroform) to give triethylammonium-3-cyanimino-4-oxo-2-(1,3,3-trimethyl-2,3-dihydro-1H-2-indolylidenmethyl)-1-cyclobuten-1-olate (19) as an oily, yellow solid. Yield: 0.96 g (78%).

$^1$H-NMR (300 MHz, DMSO-d$_6$), δ, ppm: 8.88 (1H, NH, broad s), 7.31 (1H, arom., d, 7.4 Hz), 7.20 (1H, arom., t, 7.8 Hz), 6.99 (1H, arom., d, 7.7 Hz), 6.91 (1H, arom., t, 7.3 Hz), 6.21 (0.5H, CH, broad s), 5.55 (0.5H, CH, broad s), 3.25 (3H, NCH$_3$, s), 3.10 (6H, N(CH$_2$CH$_3$)$_3$, m), 1.56 (6H, (CH$_3$)$_2$, s), 1.18 (9H, N(CH$_2$CH$_3$)$_3$, t, 7.3 Hz). FAB-MS (in NBA) m/e M$^+$ for C$_{23}$H$_{30}$N$_4$O$_2$, calculated: 394.5, found: 394. IR (KBr), ν, cm$^{-1}$: 2184, 2288 (CN), 1756 (C=O). λ$_{max}$ (abs) 435 nm (ethanol).

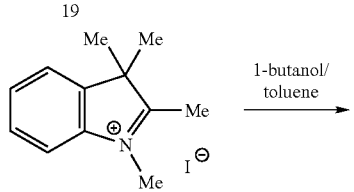

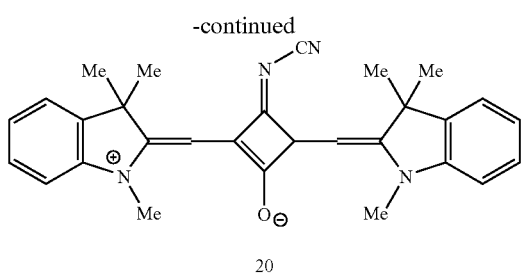

20

A mixture of 80 mg (0.203 mmol) triethylammonium 3-cyanoimino-4-oxo-2-(1,3,3-trimethyl-2,3-dihydro-1H-2-indolylidenmethyl)-1-cyclobuten-1-olate (19) and 70 mg (0.232 mmol) 1,2,3,3-tetramethyl-3H-indolium iodide is refluxed for 10 h in a mixture of 12 ml of 1-butanol and 10 ml of toluene with Dean-Stark trap. The solvent is removed under reduced pressure by a rotary evaporator. The residue is column purified and separated from the co-product 8 (Silica gel 60, 0–0.7% methanol-chloroform). A green crystalline product 20 is obtained. $R_f$=0.39 (SORBFIL, chloroform-methanol, 50:1).

$^1$H-NMR (300 MHz, DMSO-$d_6$), δ, ppm: 7.49 (2H, arom., d, 7.5 Hz), 7.36 (2H, arom., d, 3.2 Hz), 7.35 (2H, arom., t, 4.7 Hz), 7.24–7.15 (2H, arom., m), 3.61 (6H, NCH$_3$, s), 1.70 (12H, (CH$_3$)$_2$, s). The —CH= protons do not appear.

FAB-MS (in NBA) m/e M$^+$ for $C_{29}H_{28}N_4O$, calculated: 448.5, found: 448. IR (KBr), ν, cm$^{-1}$: 2156, 2192 (CN). $\lambda_{max}$ (abs) 655 nm (chloroform).

b) Synthesis of sulfo-dye (21)

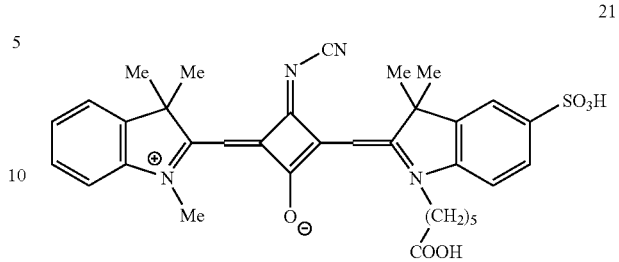

21

A mixture of 300 mg (0.76 mmol) triethylammonium 3-cyanoimino-4-oxo-2-(1,3,3-trimethyl-2,3-dihydro-1H-2-indolylidenmethyl)-1-cyclobuten-1-olate (19) and 420 mg (0.77 mmol) of 1-(5-carboxypentyl)-2,3,3-trimethyl-3H-5-indoliumsulfonate (1a) containing 35% KBr is refluxed for 8 h in a mixture of 15 ml of 1-butanol and 10 ml of toluene. The solvent is removed under reduced pressure. 20 ml of 0.1 N hydrochloric acid solution is added to the residue and the mixture is refluxed for 1 h. After cooling, the solvent is evaporated and the residue is twice purified by column chromatography. First purification is done by Silica gel 60, 10–100% methanol-chloroform. The second column is Silica gel 60 RP-18, 20–75% methanol-water. A blue crystalline product 21 is obtained.

$^1$H-NMR (200 MHz, DMSO-$d_6$), δ, ppm: 7.70 (1H, arom., s), 7.62 (1H, arom., d, 8.2 Hz), 7.55 (1H, arom., d, 7.3 Hz), 7.41 (1H, arom., d, 4.3 Hz), 7.36 (1H, arom., t, 7.6 Hz), 7.32 (1H, arom., t, 7.5 Hz), 7.31 (1H, arom., d, 7.4 Hz), 6.55 (1H, CH, s), 6.51 (1H, CH, s), 3.98 (2H, NCH$_2$, t, 6.5 Hz), 3.61 (3H, NCH$_3$, s), 2.26 (2H, CH$_2$, t, 7.4 Hz), 1.69 (12H, (CH$_3$)$_2$, s), 1.77–1.11 (6H, m). $\lambda_{max}$ (abs) 657 nm (ethanol).

Synthesis of the Cyanimino-squaraine dye (22)

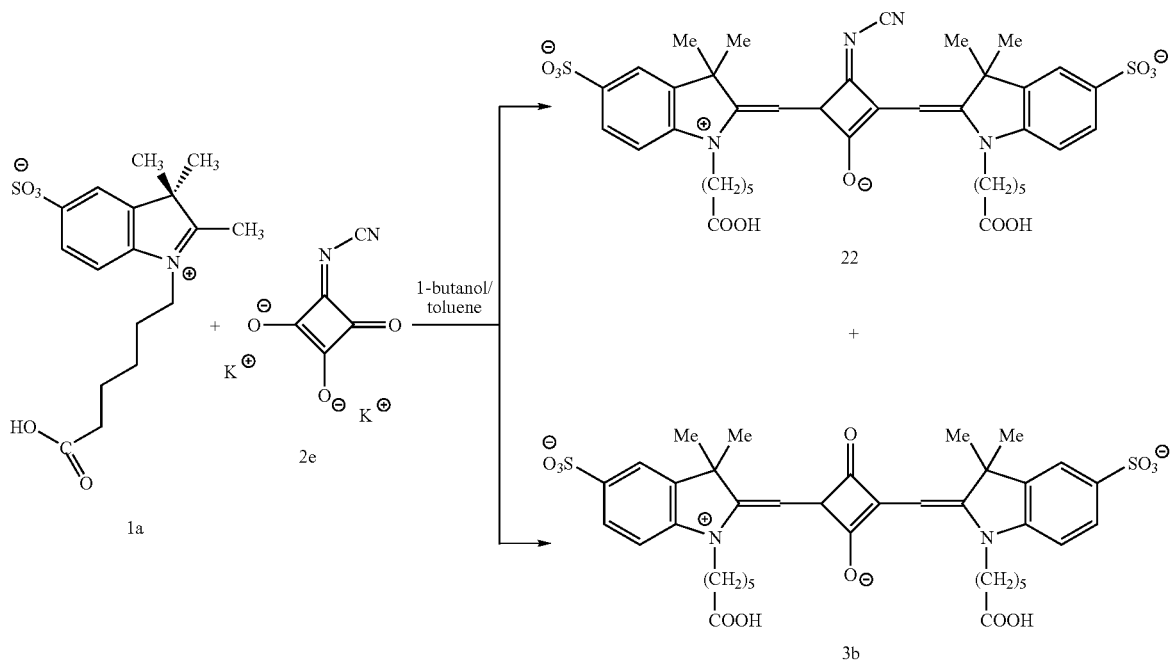

A mixture of 100 mg (0.5 mmol) of dipotassium 3-cyanoimino-4-oxo-1-cyclobutene-1,2-diolate (2e) and 550 mg (1.0 mmol) of 1-(5-carboxypentyl)-2,3,3-trimethyl-3H-5-indoliumsulfonate (1a) containing 35% KBr is refluxed for 25 h in 20 ml of glacial acetic acid. The product is precipitated by ether and isolated. The residue is column purified (Silica gel 60 RP-18, methanol-water, 1:5 v/v to give crystalline dye 3b, then product 23 is isolated using methanol-water, 2:3 v/v.

UV product 22: $\lambda_{max}$ (abs) 636 nm (water).
UV product 3b: $\lambda_{max}$ (abs) 634 nm (water).

EXAMPLE 11

Synthesis of the Hydroxyimino-squaraine dye (23)

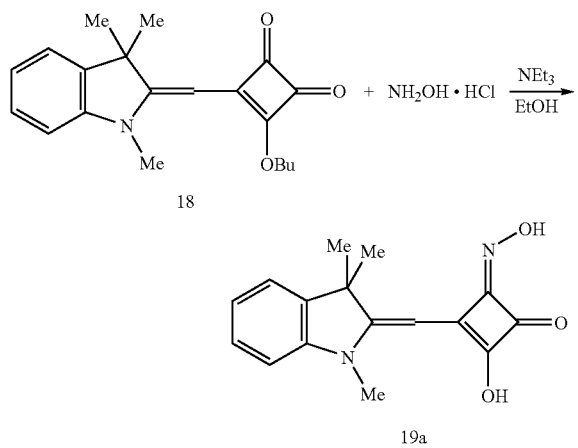

A mixture of 200 mg (0.61 mmol) of 3-butoxy-4-(1,3,3-trimethyl-2,3-dihydro-1H-2-indolylidenmethyl)-3-cyclobutene-1,2-dione (18), 50 mg (0.72 mmol) of hydroxylamine hydrochloride and 90 μl (0.64 mmol) of triethylamine is stirring in 8 ml of absolute ethanol at room temperature for 1 h and 30 min at 40° C. The solvent is removed under reduced pressure by a rotary evaporator. The obtained residue is column purified (Silica gel 60, 0–10% methanol-chloroform) to give 2-hydroxy-4-hydroxyimino-3-(1,3,3-trimethyl-2,3-dihydro-1H-2-indolylidenmethyl)-2-cyclobuten-1-one (19a) as an yellow solid. Yield: 80 mg (46%).

$\lambda_{max}$ (abs)=435 nm (ethanol).

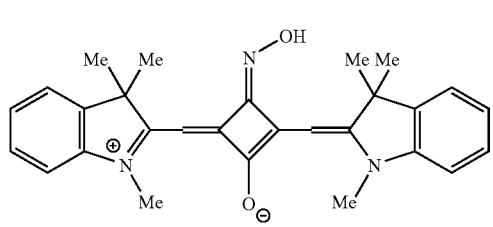

A mixture of 60 mg (0.21 mmol) 2-hydroxy-4-hydroxyimino-3-(1,3,3-trimethyl-2,3-dihydro-1H-2-indolylidenmethyl)-2-cyclobuten-1-one (19a) and 90 mg (0.30 mmol) 1,2,3,3-tetramethyl-3H-indolium iodide is refluxed for 11 h in 20 ml 1-butanol-toluene (1:1 v/v) using a Dean-Stark trap. The solvent is removed under reduced pressure. The residue is column purified (Silica gel 60, methanol-chloroform). A blue crystalline product is obtained.

$\lambda_{max}$ (abs): 647 nm (chloroform).

EXAMPLE 12

Synthesis of the symmetrical dye 24

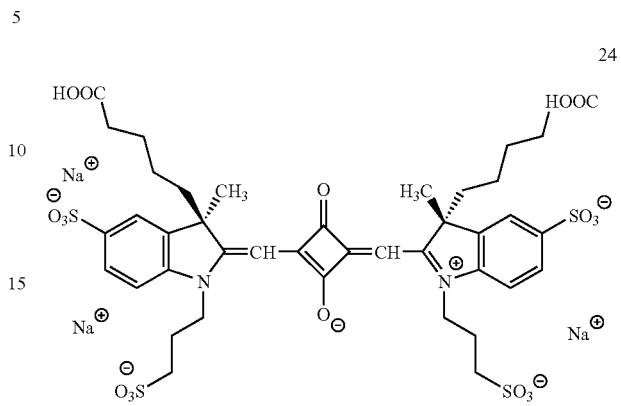

1.00 mmol of squaric acid (2a) and 2.1 mmol of 3-(5-carboxypentyl)2,3-dimethyl-5-sulfo-1-(3-sulfopropyl)indolium, sodium salt (1d) are suspended in in 50 mL of 1-butanol:toluene (1:1, v:v) and the resulting mixture was refluxed for 15–20 hours using a Dean-Stark trap filled with 4Å molecular sieve. After the mixture was cooled, and the product was purified with column chromatography using RP-18 and methanol:water as eluent to give 24.

$\lambda_{max}$(abs) 635 nm (in water).

The NHS ester is synthesized according to Example 2.

EXAMPLE 13

Synthesis of the asymmetric dye 26

1.2 mmol sodium butylate are added dropwise to an ice-cooled suspension of 1.2 mmol of squaric acid dibutyl ester (2b) and 1 mmol of 3-(5-carboxypentyl)2,3-dimethyl-5-sulfo-1-(3-sulfopropyl)indolium, sodium salt (1d) in 20–25 ml of BuOH. After stirring for 1 hour at around 0° C. the mixture is stirred for 2.5 hours at 45–50° C. and the solvent is removed under reduced pressure and the residue is purified by column chromatography (RP-18, methanol-water) to yield product 25.

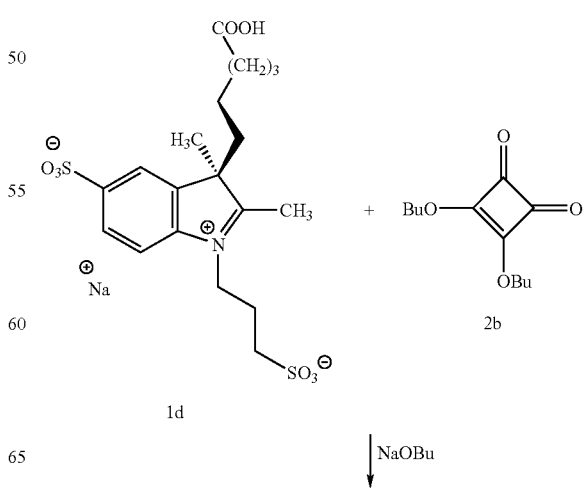

39

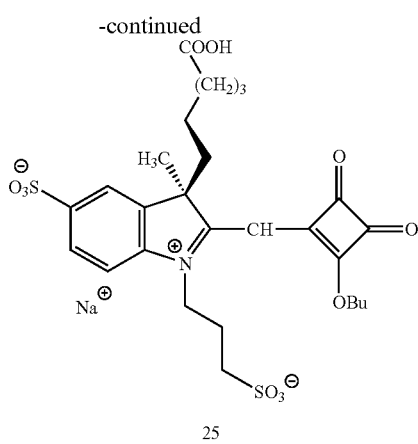

25

1 mmol of 25 and 1.2 mmol of the indolenine 1h are refluxed in 50 mL BuOH/toluene for 8 hours using a Dean-Stark trap. The solvent is removed under reduced pressure and the residue is purified by column chromatography (RP-18, methanol-water) to yield compound 26.

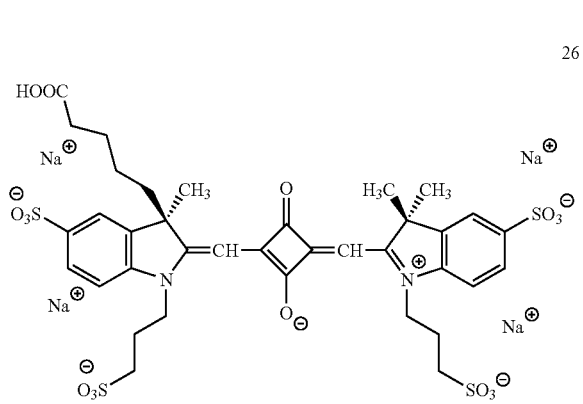

26

EXAMPLE 14

Example 14 shows squaraine dyes with different functional groups in position 3:

In some embodiments, the dye contains a large number of sulfonic acid groups (up to 7) and up to 6 spacers groups; increasing the number of ionic and spacer groups may help to prevent dye aggregation and increase the quantum yields in aqueous solution and when bound to proteins. (Gruber et al. Bioconj. Chem. 2000, 11, 696–704). Sulfonate groups may also be introduced by reaction of a 3-carboxy-alkyl-substituted compound with taurine according to Terpetschnig et al. Anal. Biochem. 217, 197–204 (1994).

In another example, water-solubility is achieved by introducing ethylene glycol spacers instead of ionic sulfonic acid groups. Polyethers provide water-solubility without increasing the charge of the molecule and thus have reduced electrostatic interaction with the environment (e.g. lower non-specific binding to proteins). Sulfonate groups can also be replaced by any other ionic group (e.g. phosphate groups, quaternary ammonium groups, among others).

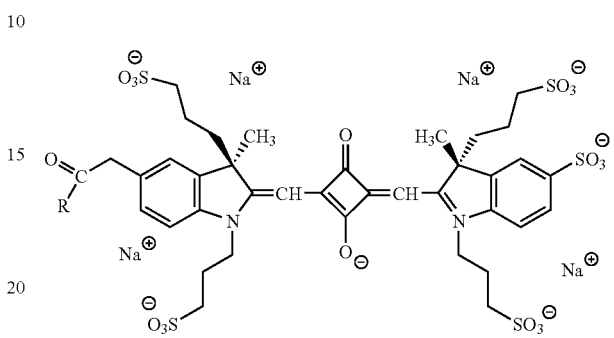

R=OH, NHS, linked carrier

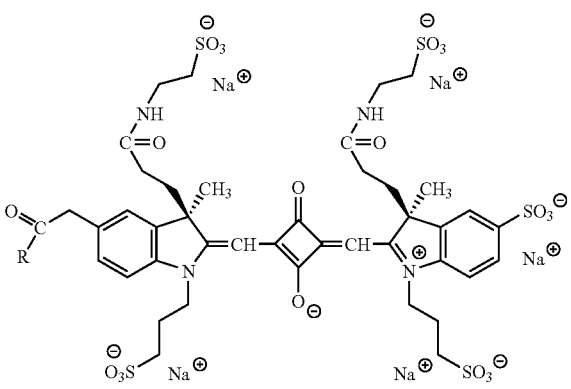

R=COOH, C(=O)—NHS, linked carrier, —N=C=S, OH, malimide, iodoacetamide, phosphoramidite among other reactive groups.

R=OH, NHS, linked carrier

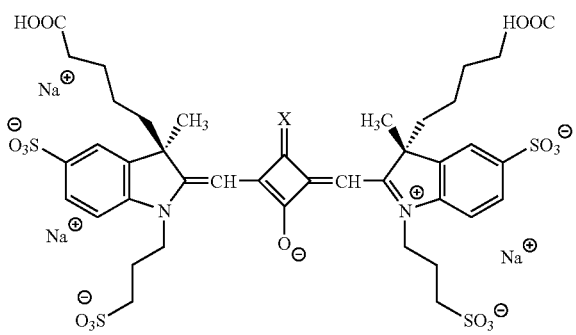

where X=C(CN)$_2$, N—CN, N—OH, N—SO$_3^-$ etc.

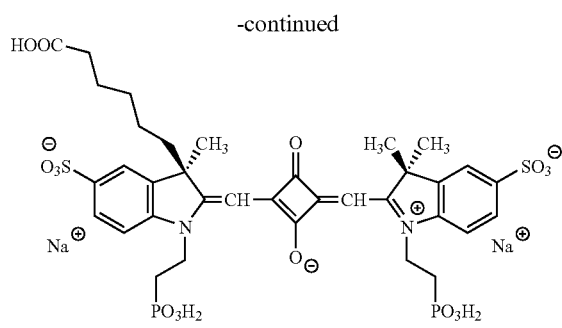

R=OH, NHS, linked carrier

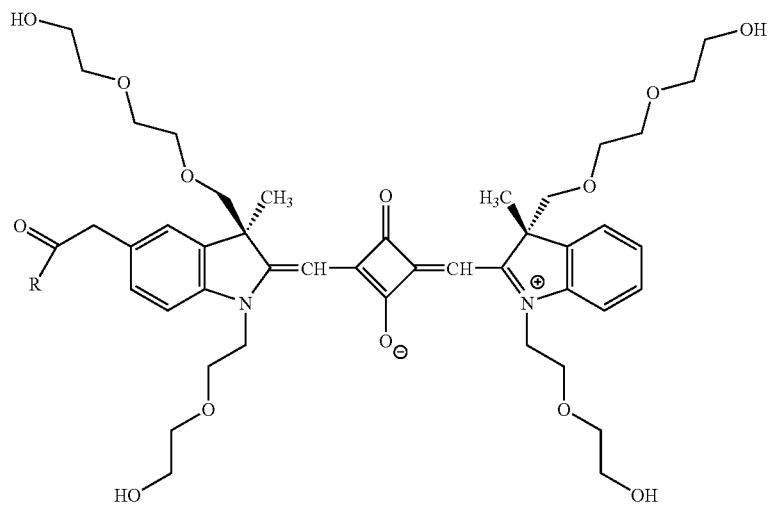

R=OH, NHS, linked carrier

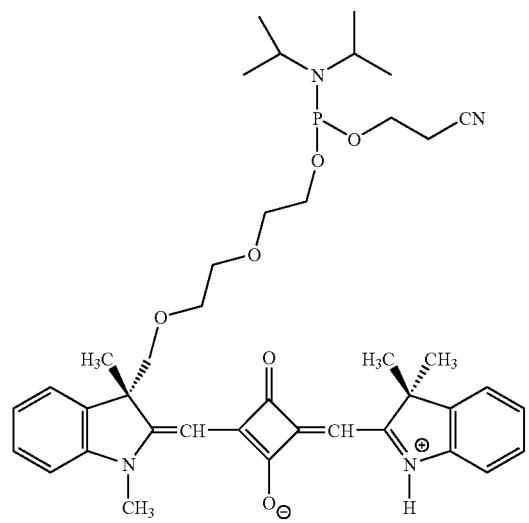

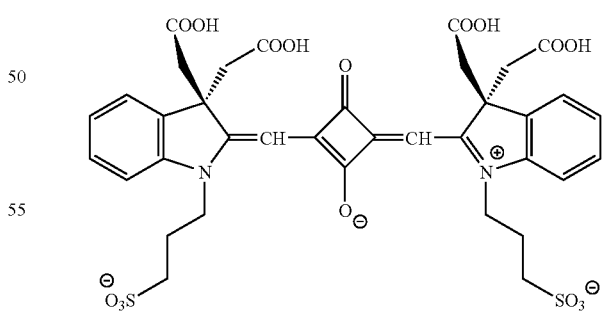

EXAMPLE 15

A reporter compound that incorporates a metal chelating group, potentially useful as a probe for one or more target metal ions.

EXAMPLE 16

General Protein Labelling Procedures and Determination of Dye-to-Protein Ratios

Protein labelling reactions were carried out using a 50 mM bicarbonate buffer (pH 9.1). A stock solution of 1 mg of dye in 100 μL of anhydrous DMF was prepared. 10 mg of protein were dissolved in 1 mL of 100 mM bicarbonate buffer (pH 9.1). Dye from the stock solution was added, and the mixture was stirred for 24 h at room temperature.

Unconjugated dye was separated from labelled proteins using gel permeation chromatography with SEPHADEX G50 (0.5 cm×20 cm column) and a 22 mM phosphate buffer solution (pH 7.3) as the eluent. The first colored band contained the dye-protein conjugate. A later blue band with a much higher retention time contained the separated free dye. A series of labelling reactions as described above were set up to obtain different dye-to-protein ratios. Compared to the free forms, the protein-bound forms of the dyes show distinct changes in their spectral properties.

Protein concentration was determined using the BCA Protein Assay Reagent Kit from Pierce (Rockford, Ill.). The dye-to-protein ratio (D/P) gives the number of dye molecules covalently bound to the protein.

Covalent attachment of NHS-ester (14) to polyclonal anti-HSA

385 μL (5.2 mg/mL) of anti-HSA were dissolved in a 750 μL bicarbonate buffer (0.1 M, pH 9.0). 1 mg of NHS-ester (14) was dissolved in 50 μL of DMF and slowly added to the above-prepared protein solution with stirring. After 20 h of stirring, the protein-conjugate was separated from the free dye using Sephadex G50 and a phosphate buffer (22 mM, pH 7.2). The first blue band that was isolated contained the labeled conjugate.

Conjugation of (14) to HSA 0.5 mg of (14) in 50 μL of DMF were slowly added to a stirred solution of 5 mg of HSA in 750 μL of bicarbonate buffer (0.1 M, pH 9.0). The mixture was stirred for another 6 h at room temperature. The mixture was dialyzed against a phosphate buffer (22 mM, pH 7.2) using a dialysis membrane (1500 FT, Union Carbid) with a cutoff of 10.000.

Analysis: $\lambda_{max}$(abs)=642 nm (PBS); $\lambda_{max}$(em)=654 nm (PBS).

Similar reactions were performed using alternative reporter compounds having reactive functional groups.

Fluorescence Decay Times of Various Dyes and their Conjugates:

The following table shows fluorescence decay times of various dyes and their conjugates. The experimental conditions included (1) excitation at 600 nm, using a rhodamine B dye laser, (2) emission observed at 660 nm, using an interference filter having a 10 nm band pass, and (3) temperature of 20° C.

| Sample | Decay time [ns] | Amplitude | Fractional Intensity | Mean [ns] | Chi square |
|---|---|---|---|---|---|
| 3a | 0.21 | 0.752 | 0.496 | 0.43 | 3.7 |
|  | 0.65 | 0.248 | 0.504 |  |  |
| 4 | 0.20 | 0.558 | 0.286 | 0.51 | 3.8 |
|  | 0.64 | 0.442 | 0.714 |  |  |
| 3b-HSA | 0.18 | 0.676 | 0.142 | 2.26 | 1.7 |
|  | 0.96 | 0.089 | 0.097 |  |  |
|  | 3.81 | 0.235 | 0.761 |  |  |
| 13-HSA | 0.11 | 0.865 | 0.036 | 2.44 | 5.22 |
|  | 0.768 | 0.068 | 0.201 |  |  |
|  | 2.99 | 0.067 | 0.764 |  |  |
| CY5 | 1.02 | 1 | 1 | 1.01 | 2.1 |
| CY5-hCG | 0.16 | 0.408 | 0.071 | 1.33 | 2.8 |
|  | 1.41 | 0.592 | 0.929 |  |  |

Spectral Properties and Dye-to-protein Ratios for Various Reactive Squaraine Dyes and their Conjugates:

Spectral properties and dye-to-protein ratios were determined for various reactive squaraine dyes and their conjugates. The following table summarizes absorption (excitation) and emission spectra data for (13)-HSA and various other reactive squaraine dyes and their conjugates in PBS.

| Squaraine | $\lambda_{max}$(abs) [nm] | $\lambda_{max}$ (em) [nm] | ε [L/(mol*cm)] | Q.Y. [%] | D/P [mol/mol] |
|---|---|---|---|---|---|
| 3b | 635 | 642 | 180.000 | 13 | — |
| 3b-HSA | 642 | 653 | — | 60–70 | 1 |
| 6a | 627 | 647 | 100.000 | 3 | — |
| 7 | 634 | 646 | 120.000 | 13 |  |
| 7-HSA | 635 | 660 | — | 50 | 0.5 |
| 13 | 630 | 649 | 150.000 | 5 | — |
| 13-HSA | 642 | 654 | — | 60–70 | 0.8 |
| 15 | 667 | 685 | 180.000 | 4 | — |
| 15-HSA | 685 | 704 | — | n.d. | n.d. |

EXAMPLE 17

Description of Applications of the Invention

The reporter compounds disclosed above exhibit utility for a variety of useful methods for various assay formats.

The assay may be a competitive assay that includes a recognition moiety, a binding partner, and an analyte. Binding partners and analytes may be selected from the group consisting of biomolecules, drugs, and polymers, among others. In some competitive assay formats, one or more components are labeled with photoluminescent compounds in accordance with the invention. For example, the binding partner may be labeled with such a photoluminescent compound, and the displacement of the compound from an immobilized recognition moiety may be detected by the appearance of fluorescence in a liquid phase of the assay. In other competitive assay formats, an immobilized enzyme may be used to form a complex with the fluorophore-conjugated substrate.

The binding of antagonists to a receptor can be assayed by a competitive binding method in so-called ligand/receptor assays. In such assays, a labeled antagonist competes with an unlabelled ligand for the receptor binding site. One of the binding partners can be, but not necessarily has to be, immobilized. Such assays may also be performed in microplates. Immobilization can be achieved via covalent attachment to the well wall or to the surface of beads.

Other preferred assay formats are immunological assays. There are several such assay formats, including competitive binding assays, in Which labeled and unlabeled antigens compete for the binding sites on the surface of an antibody (binding material). Typically, there are incubation times required to provide sufficient time for equilibration. Such assays can be performed in a heterogeneous or homogeneous fashion.

Sandwich assays may use secondary antibodies and excess binding material may be removed from the analyte by a washing step.

Other types of reactions include binding between avidin and biotin, protein A and immunoglobulins, lectins and sugars (e.g., concanavalin A and glucose).

The reporter compounds described here also may be used to sequence nucleic acids and peptides. For example, fluorescently-labeled oligonucleotides may be used to trace DNA fragments. Other applications of labeled DNA primers include fluorescence in-situ hybridization methods (FISH) and for single nucleotide polymorphism (SNIPS) applications, among others.

Multicolor labeling experiments may permit different biochemical parameters to be monitored simultaneously. For this purpose, two or more reporter compounds are introduced into the biological system to report on different biochemical functions. The technique can be applied to fluorescence in-situ hybridization (FISH), DNA sequencing, fluorescence microscopy, and flow cytometry. One way to achieve multicolor analysis is to label biomolecules such as nucleotides, proteins or DNA primers with different luminescent reporters having distinct luminescence properties. Luminophores with narrow emission bandwidths are preferred for multicolor labeling, because they have only a small overlap with the other dyes and hence increase the number of dyes possible in a multicolor experiment. Importantly, the emission maxima have to be well separated from each other to allow sufficient resolution of the signal. A suitable multicolor triplet of fluorophores would include Cy3, TRITC, and a photoluminescent compound as described herein, among others.

The simultaneous use of FISH (fluorescence in-situ hybridization) probes in combination with different fluorophores is useful for the detection of chromosomal translocations, for gene mapping on chromosomes, and for tumor diagnosis, to name only a few applications. One way to achieve simultaneous detection of multiple sequences is to use combinatorial labeling. Up to seven different DNA targets can be simultaneously visualized by using a combination of haptenated DNA probes (e.g. biotin, digoxigenin or dinitrophenol) with three sets of distinguishable fluorophores showing emission in the green (fluorescein), red (Texas Red), and blue (7-amino-4-methyl-coumarin-3-acidic acid or Cascade Blue) (Ried, T. et al., Proc. Natl. Acad. Aci. USA 89:1388–1392, (1992). Three labeled DNA probes can be visualized by the distinct spectra of the three fluorescent markers, while four others will appear as fluorophore mixtures, e.g. probe 4 (fluorescein and rhodamine); probe 5 (fluorescein and Cascade Blue); probe 6 (rhodamine and cascade Blue); and probe 7 (fluorescein, rhodamine and Cascade Blue).

The second way is to label each nucleic acid probe with a luminophore with distinct spectral properties. Similar conjugates can be synthesized from this invention and used in a multicolor multisequence analysis approach.

The reporter compounds of the invention tan also be used for screening assays for a combinatorial library of compounds. The compounds can be screened for a number of characteristics, including their specificity and avidity for a particular recognition moiety.

Assays for screening a library of compounds are well known. A screening assay is used to determine compounds that bind to a target molecule, and thereby create a signal change which is generated by a labeled ligand bound to the target molecule. Such assays allow screening of compounds that act as agonists or antagonists of a receptor, or that disrupt a protein-protein interaction. It also can be used to detect hybridization pr binding of DNA and/or RNA.

Other screening assays are based on compounds that affect the enzyme activity. For such purposes, quenched enzyme substrates of the invention could be used to trace the interaction with the substrate. In this approach, the cleavage of the fluorescent substrate leads to a change in the spectral properties such as the excitation and emission maxima, intensity and/or lifetime, which allows to distinguish between the free and the bound luminophore.

The reporter compounds disclosed above may also be relevant to single molecule fluorescence microscopy (SMFM) where detection of single probe molecules depends on the availability of a fluorophore with high fluorescence yield, high photostability, and long excitation wavelength.

There may be limitations in some instances to the use of the above compounds as labels. For example, typically only a limited number of dyes may be attached to a biomolecules without altering the fluorescence properties of the dyes (e.g. quantum yields, lifetime, emission characteristics, etc.) and/or the biological activity of the bioconjugate. Typically quantum yields may be reduced at higher degrees of labeling. Encapsulation into beads offers a means to overcome the above limitation for the use of such compounds as fluorescent markers. Fluorescent beads and polymeric materials are becoming increasingly attractive as labels and materials for bioanalytical and sensing applications. Various companies offer particles with defined sizes ranging from nanometers to micrometers. Noncovalent encapsulation in beads may be achieved by swelling the polymer in an organic solvent, such as toluene or chloroform, containing the dye. Covalent encapsulation may be achieved using appropriate reactive functional groups on both the polymer and the dyes. In general, hydrophobic versions of the invention may be used for non-covalent encapsulation in polymers, and one or more dyes could be introduced at the same time. Surface-reactive fluorescent particles allow covalent attachment to molecules of biological interest, such as antigens, antibodies, receptors etc.

Compounds of this invention may also be attached to the surface of metallic nanoparticles such as gold or silver nanoparticles. It has recently been demonstrated that fluorescent molecules may show increased quantum yields near metallic nanostructures e.g. gold or silver nanoparticles (O. Kulakovich et al. Nanoletters 2 (12) 1449–52, 2002). This enhanced fluorescence may be attributable to the presence of a locally enhanced electromagnetic field around metal nanostructures. The changes in the photophysical properties Of a fluorophore in the vicinity of the metal surface may be used to develop novel assays and sensors. In one example the nanoparticle may be labeled with one member of a specific binding pair (antibody, protein, receptor etc) and the complementary member (antigen, ligand) may be labeled with a fluorescent molecule in such a way that the interaction of both binding partners leads to an detectable change in one or more fluorescence properties (such as intensity, quantum yield, lifetime, among others). Replacement of the labeled binding partner from the metal surface may lead to a change in fluorescence, that can then be used to detect and/or quantify an analyte.

Gold colloids can be synthesized by citrate reduction of a diluted aqueous $HAuCl_4$ solution. These gold nanoparticles are negatively charged due to chemisorption of citrate ions. Surface functionalization may be achieved by reacting the nanoparticles with thiolated linker groups containing amino or carboxy functions. In another approach, thiolated biomolecules are used directly for coupling to these particles.

In recent studies (T. Fare et al., Anal. Chem. 75(17), 4672–4675, 2003) researchers made an observation that the fluorescence signals of cyanine dyes such as CY5 dye and the ALEXA 647 dyes in microarrays are strongly dependent on the concentration of ozone during posthybridization array washing. Controlled exposures of microarrays to ozone confirmed this factor as the root cause, and showed the susceptibility of a class of cyanine dyes (e.g., CY5 dyes, ALEXA 647 dyes) to ozone levels as low as 5–10 ppb for periods as short as 10–30 s.

One of the significant findings was the low dose level (ozone concentration multiplied by exposure time) that could induce the onset of the phenomenon, suggesting many labs may be at risk. For example, it is not uncommon that the environmental ozone levels would exceed 60 ppb during peak traffic hours on a sunny summer afternoon. Reporter compounds present on or in arrays that are exposed to these levels for as short as 1 min may begin to show significant degradation in a typical laboratory setting.

There are ways that help to eliminate the occurrence of ozone effects on microarrays, for example, equipping laboratories with HVAC systems having filters to significantly reduce ozone levels, or the use of dye-protecting solutions to avoid signal degradation. However, each of these approaches may add additional costs and/or time to perform the assay. These findings Suggest the need for dyes and labels in the 600 to 700 nm wavelength range with improved chemical and photochemical stability.

Experimental data on squaraine dyes indicate that introduction of electron-withdrawing groups into the dye backbone may increase the photostability of such dyes. In addition it has been found that ring-substitution of squaraine dyes in the central squaraine ring with electron-withdrawing groups may lead to dyes with exceptional photostabilities.

Analytes

The invention may be used to detect an analyte that interacts with a recognition moiety in a detectable manner. As such, the invention can be attached to a recognition moiety which is known to those of skill in the art. Such recognition moieties allow the detection of specific analytes. Examples are pH-, or potassium sensing molecules, e.g., synthesized by introduction of potassium chelators such as crown-ethers (aza crowns, thia crowns etc). Calcium-sensors based on the BAPTA (1,2-Bis(2-aminophenoxy)ethan-N,N,N',N'-tetra-aceticacic) chelating moiety are frequently used to trace intracellular ion concentrations. The combination of a compound of the invention and the calcium-binding moiety BAPTA may lead to new long-wavelength absorbing and emitting Ca-sensors which could be used for determination of intra- and extracellular calcium concentrations (Akkaya et al. Tetrahedron Lett. 38:4513–4516 (1997). Additionally, or in the alternative, reporter compounds already having a plurality of carboxyl functional groups, as shown in Example 15, may be directly used for sensing and/or quantifying physiologically and environmentally relevant ions.

Fluorescence Methods

The disclosed reporter compounds may be detected using common intensity-based fluorescence methods. The squaraine dyes are known to have lifetimes in the range of hundreds of ps to a few ns (see Example 16). The nanosecond lifetime and long-wavelength absorption and emission of these dyes when bound to proteins may allow them to be measured using relatively inexpensive instrumentation that employs laser diodes for excitation and avalanche photodiodes for detection. Typical assays based on the measurement of the fluorescence lifetime as a parameter include for example FRET (fluorescence resonance energy transfer) assays. The binding between a fluorescent donor labeled species (typically an antigen) and a fluorescent acceptor labeled species may be accompanied by a change in the intensity and the fluorescence lifetime. The lifetime can be measured using intensity- or phase-modulation-based methods (J. R. LAKOWICZ, PRINCIPLES OF FLUORESCENCE SPECTROSCOPY ($2^{nd}$ Ed. 1999)).

Squaraine dyes exhibit high intrinsic polarization in the absence of rotational motion, making them useful as tracers in fluorescence polarization (FP) assays. Fluorescence polarization immunoassays (FPI) are widely applied to quantify low molecular weight antigens. The assays are based on polarization measurements of antigens labeled with fluorescent probes. The requirement for polarization probes used in FPIs is that emission from the unbound labeled antigen be depolarized and increase upon binding to the antibody. Low molecular weight species labeled with the compounds of the invention can be used in such binding assays, and the unknown analyte concentration can determined by the change in polarized emission from the fluorescent tracer molecule.

Compositions and Kits

The invention also provides compositions, kits and integrated systems for practicing the various aspects and embodiments of the invention, including producing the novel compounds and practicing of assays. Such kits and systems may include a reporter compound as described above, and may optionally include one or more of solvents, buffers, calibration standards, enzymes, enzyme substrates, and additional reporter compounds having similar or distinctly different optical properties.

Although the invention has been disclosed in preferred forms, the specific embodiments thereof as disclosed and illustrated herein are not to be considered in a limiting sense, because numerous variations are possible. Applicant regards the subject matter of his invention to include all novel and nonobvious combinations and subcombinations of the various elements, features, functions, and/or properties disclosed herein. No single element, feature, function, or property of the disclosed embodiments is essential. The following claims define certain combinations and subcombinations of elements, features, functions, and/or properties that are regarded as novel and nonobvious. Other combinations and subcombinations may be claimed through amendment of the present claims or presentation of new claims in this or a related application. Such claims, whether they are broader, narrower, or equal in scope to the original claims, also are regarded as included within the subject matter of applicant's invention.

What is claimed is:

1. A composition of matter comprising a photoluminescent compound, the photoluminescent compound having a four-, five-, or six-member aromatic ring Z, with substituents A, B, C, D, E, and F, according to the formula:

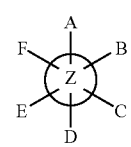

wherein F is absent when Z is a five-member ring, and wherein E and F are absent when Z is a four-member ring;
wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged:

when the A substituent is neutral, A is =O; when the A substituent is negatively charged, A is —O⁻;

where each D, E, and F substituent, when present and neutral, is independently selected from the group consisting of =O, =S, =Se, =Te, =N—R^c, and =C(R^f)(R^g), wherein each of R^c is selected from the group consisting of aliphatic, heteroatom-substituted aliphatic, polyether, aromatic, reactive aliphatic, and reactive aromatic groups, hydrogen, CN, OH, SO₃H, and COO-R^m, where R^m, is selected from a group consisting of hydrogen, aliphatic substituents, aromatic substituents, reactive aliphatic substituents, reactive aromatic substituents, and linked carriers, and where R^f and R^g, are selected from the group consisting of carboxylic acid, cyano, carboxamide, carboxylic ester, and aliphatic amine groups, or, alternatively, or in addition, R^f and R^g, taken in combination, may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —O⁻, —S⁻, —Se⁻, —Te⁻, —(N—R^c)⁻, and —(C(R^f)(R^g))⁻;

each B and C substituent is selected from the group consisting of W¹ and W², wherein W¹ and W² have the respective formulae

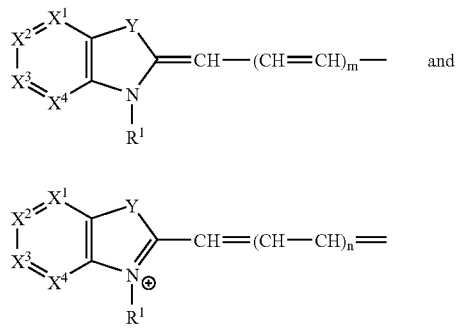

where each B and C substituent is W¹ if B and C are adjacent on Z, and one of B and C is W¹ and the other of B and C is W² if B and C are separated by one of A, D, E, and F on ring Z;

m and n are independently selected from the group consisting of 0, 1, and 2;

each Y is independently selected for each of B and C from the group consisting of O, S, N—R^h, and C(R^i)(R^j), wherein R^h is selected from the group consisting of H, aliphatic groups, alicyclic groups, aromatic groups, spacers bound to ionic and reactive groups, and R^i and R^j are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or R^i and R^j taken in combination form a ring-system that is optionally further substituted by one or more reactive or ionic substituents; provided that at least one Y is C(R^i)(R^j), at least one of R^c, R^f, R^g, R^i or R^j includes a reactive group, a linked carrier, or an ionic substituent capable of increasing the hydrophilicity of the entire compound; and wherein at least one of R^i and R^j includes a reactive group selected for reacting with amine moieties from the group consisting of N-hydroxysuccinimidyl esters, isothiocyanates, and sulfonylhalogenides;

each R¹ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of X¹, X², X³, and X⁴ is independently selected for each of B and C from the group consisting of N, O, S, and C—R^k, wherein R^k is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

2. A composition of matter comprising a photoluminescent compound, the photoluminescent compound having a four-, five-, or six-member aromatic ring Z, with substituents A, B, C, D, E, and F, according to the formula:

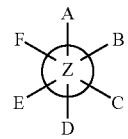

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is =O; when the A substituent is negatively charged, A is —O⁻;

where each D, E, and F substituent, when present and neutral, is independently selected from the group consisting of =O, =S, =Se, =Te, =N—R^c, and =C(R^f)(R^g), wherein each of R^c is selected from the group consisting of aliphatic, heteroatom-substituted aliphatic, polyether, aromatic, reactive aliphatic, and reactive aromatic groups, hydrogen, CN, OH, SO₃H, and COO—R^m, where R^m is selected from a group consisting of hydrogen, aliphatic substituents, aromatic substituents, reactive aliphatic substituents, reactive aromatic substituents, and linked carriers, and where R^f and R^g are selected from the group consisting of carboxylic acid, cyano, carboxamide, carboxylic ester, and aliphatic amine groups, or, alternatively, or in addition, R^f and R^g, taken in combination, may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —O⁻, —S⁻, —Se⁻, —Te⁻, —(N—R^c)⁻, and —(C(R^f)(R^9));

each B and C substituent is selected from the group consisting of W¹ and W², wherein W¹ and W² have the respective formulae

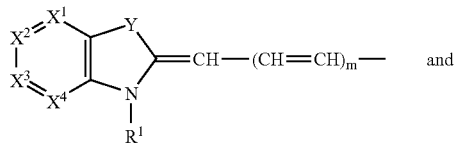

and

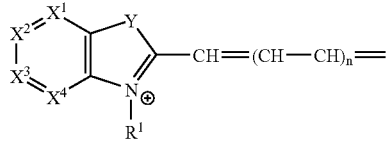

where each B and C substituent is W¹ if B and C are adjacent on Z, and one of B and C is W¹ and the other of B and C is W² if B and C are separated by one of A, D, E, and F on ring Z;

m and n are independently selected from the group consisting of 0, 1, and 2;

each Y is independently selected for each of B and C from the group consisting of O, S, N—R^h, and C(R^i)(R^j), wherein R^h is selected from the group consisting of H, aliphatic groups, alicyclic groups, aromatic groups, spacers bound to ionic and reactive groups, and R^i and R^j are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or R^i and R^j taken in combination form a ring-system that is optionally further substituted by one or more reactive or ionic substituents; provided that at least one Y is C(R^i)(R^j), at least one of R^c, R^f, R^g, R^i or R^j includes a reactive group, a linked carrier, or an ionic substituent capable of increasing the hydrophilicity of the entire compound; and wherein at least one of R^i and R^j includes a reactive group selected for reacting with thiol moieties from the group consisting of iodoacetamides and maleimides;

each R¹ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of X¹, X², X³, and X⁴ is independently selected for each of B and C from the group consisting of N, O, S, and C—R^k, wherein R^k is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

3. A composition of matter comprising a photoluminescent compound, the photoluminescent compound having a four-, five-, or six-member aromatic ring Z, with substituents A, B, C, D, E, and F, according to the formula:

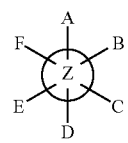

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is =O; when the A substituent is negatively charged, A is —O⁻;

where each D, E, and F substituent, when present and neutral, is independently selected from the group consisting of =O, =S, =Se, =Te, =N—R^c, and =C(R^f)(R^g), wherein each of R^c is selected from the group consisting of aliphatic, heteroatom-substituted aliphatic, polyether, aromatic, reactive aliphatic, and reactive aromatic groups, hydrogen, CN, OH, SO₃H, and COO—R^m, where R^m is selected from a group consisting of hydrogen, aliphatic substituents, aromatic substituents, reactive aliphatic substituents, reactive aromatic substituents, and linked carriers, and where R^f and R^g are selected from the group consisting of carboxylic acid, cyano, carboxamide, carboxylic ester, and aliphatic amine groups, or, alternatively, or in addition, R^f and R^g, taken in combination may form 5- and 6-membered rings that include, but are not limited to, pyrazolidine-dione, barbituric acid, thiobarbituric acid, isoxazolone, pyrazolone, pyridone, rhodanine. pyrrolotriazole, and pyrazolotriazole rings;

D, E, and F, when present and negatively charged, are independently selected from the group consisting of —O⁻, —S⁻, —Se⁻, —Te⁻, —(N—R^c)⁻, and —(C(R^f)(R^g))⁻;

each B and C substituent is selected from the group consisting of W¹ and W², wherein W¹ and W² have the respective formulae

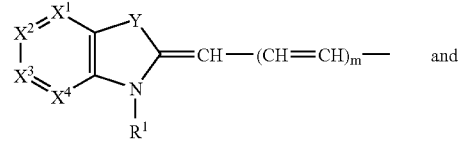

and

-continued

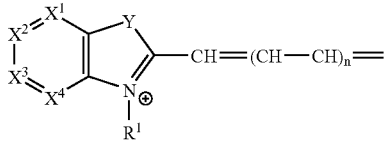

where each B and C substituent is $W^1$ if B and C are adjacent on Z, and one of B and C is $W^1$ and the other of B and C is $W^2$ if B and C are separated by one of A, D, E, and F on ring Z;

m and n are independently selected from the group consisting of 0, 1, and 2;

each Y is independently selected for each of B and C from the group consisting of O, S, N—$R^h$, and $C(R^i)(R^j)$, wherein $R^h$ is selected from the group consisting of H, aliphatic groups, alicyclic groups, aromatic groups, spacers bound to ionic and reactive groups, and $R^i$ and $R^j$ are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or $R^i$ and $R^j$ taken in combination form a ring-system that is optionally further substituted by one or more reactive or ionic substituents; provided that at least one Y is $C(R^i)(R^j)$, at least one of $R^c$, $R^f$, $R^g$, $R^i$ or $R^j$ includes a reactive group, a linked carrier, or an ionic substituent capable of increasing the hydrophilicity of the entire compound; and wherein at least one of $R^i$ and $R^j$ includes a reactive group selected for reacting with nucleic acids from the group consisting of phosphoramidites;

each $R^1$ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of N, O, S, and C—$R^k$, wherein $R^k$ is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

4. A composition of matter comprising a photoluminescent compound, the photoluminescent compound having a four-, five-, or six-member aromatic ring Z, with substituents A, B, C, D, E, and F, according to the formula:

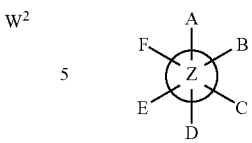

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is =O; when the A substituent is negatively charged, A is —O⁻;

where each D, E, and F substituent, when present and neutral, is independently selected from the group consisting of =O, =S, =Se, =Te, =N—$R^c$, and =$C(R^f)(R^g)$, wherein each of $R^c$ is selected from the group consisting of aliphatic, heteroatom-substituted aliphatic, polyether, aromatic, reactive aliphatic, and reactive aromatic groups, hydrogen, CN, OH, $SO_3H$, and COO—$R^m$, where $R^m$ is selected from a group consisting of hydrogen, aliphatic substituents, aromatic substituents, reactive aliphatic substituents, reactive aromatic substituents, and linked carriers, and where $R^f$ and $R^g$ are selected from the group consisting of carboxylic acid, cyano, carboxamide, carboxylic ester, and aliphatic amine groups, or, alternatively, or in addition, $R^f$ and $R^g$, taken in combination, may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —O⁻, —S⁻, —Se⁻, —Te⁻, —(N—$R^c$)⁻, and —$(C(R^f)(R^g))$⁻;

each B and C substituent is selected from the group consisting of $W^1$ and $W^2$, wherein $W^1$ and $W^2$ have the respective formulae

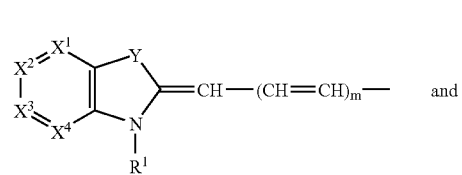

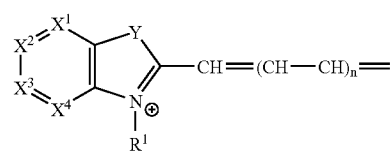

where each B and C substituent is $W^1$ if B and C are adjacent on Z, and one of B and C is $W^1$ and the other of B and C is $W^2$ if B and C are separated by one of A, D, E, and F on ring Z;

m and n are independently selected from the group consisting of 0, 1, and 2;

each Y is independently selected for each of B and C from the group consisting of O, S, N—$R^h$, and $C(R^i)(R^j)$, wherein $R^h$ is selected from the group consisting of H, aliphatic groups, alicyclic groups, aromatic groups, spacers bound to ionic and reactive groups, and $R^i$ and $R^j$ are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or $R^i$ and $R^j$ taken in combination form a ring-system that is optionally further substituted by one or more reactive or ionic substituents; provided that at least one Y is $C(R^i)(R^j)$, at least one of $R^c$, $R^f$, $R^g$, $R^i$ or $R^j$ includes a reactive group, a linked carrier, or an ionic substituent capable of increasing the hydrophilicity of the entire compound; and wherein at least one of $R^i$ and $R^j$ includes a linked carrier;

each $R^1$ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of N, O, S, and C—$R^k$, wherein $R^k$ is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine.

5. A composition of matter comprising a photoluminescent compound, the photoluminescent compound having a four-, five-, or six-member aromatic ring Z, with substituents A, B, C, D, E, and F, according to the formula;

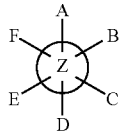

wherein F is absent when Z is a five-member ring, and wherein E and F are absent when Z is a four-member ring;
wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;
when the A substituent is neutral, A is =O; when the A substituent is negatively charged, A is —O⁻;
where each D, E, and F substituent, when present and neutral, is independently selected from the group consisting of =O, =S, =Se, =Te, =N—$R^c$, and =$C(R^f)(R^g)$, wherein each of $R^c$ is selected from the group consisting of aliphatic, heteroatom-substituted aliphatic, polyether, aromatic, reactive aliphatic, and reactive aromatic groups, hydrogen, CN, OH, $SO_3H$, and COO—$R^m$, where $R^m$ is selected from a group consisting of hydrogen, aliphatic substituents, aromatic substituents, reactive aliphatic substituents, reactive aromatic substituents, and linked carriers, and where $R^f$ and $R^g$ are selected from the group consisting of carboxylic acid, cyano, carboxamide, carboxylic ester, and aliphatic amine groups, or, alternatively, or in addition, $R^f$ and $R^g$ taken in combination, may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —O⁻, —S⁻, —Se⁻, —Te⁻, —(N—$R^c$)⁻, and —$(C(R^f)(R^g))^-$;

each B and C substituent is selected from the group consisting of $W^1$ and $W^2$, wherein $W^1$ and $W^2$ have the respective formulae

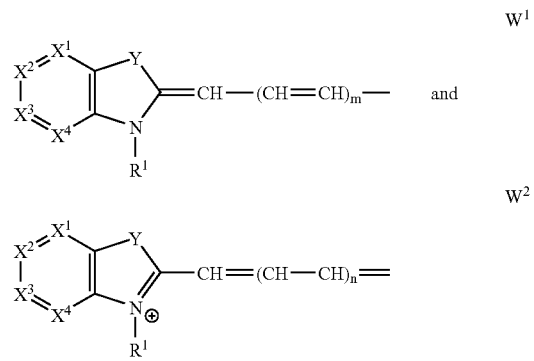

where each B and C substituent is $W^1$ if B and C are adjacent on Z, and one of B and C is $W^1$ and the other of B and C is $W^2$ if B and C are separated by one of A, D, E, and F on ring Z;

m and n are independently selected from the group consisting of 0, 1, and 2;

each Y is independently selected for each of B and C from the group consisting of O, S, N—$R^h$, and $C(R^i)(R^j)$, wherein $R^h$ is selected from the group consisting of H, aliphatic groups, alicyclic groups, aromatic groups, spacers bound to ionic and reactive groups, and $R^i$ and $R^j$ are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or $R^i$ and $R^j$ taken in combination form a ring-system that is optionally further substituted by one or more reactive or ionic substituents; provided that at least one Y is $C(R^i)(R^j)$, at least one of $R^c$, $R^f$, $R^g$, $R^i$ or $R^j$ includes a reactive group, a linked carrier, or an ionic substituent capable of increasing the hydrophilicity of the entire compound;

each $R^1$ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of N, O, S, and C—$R^k$, wherein $R^k$ is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring;

each H may be independently replaced by a fluorine; and wherein at least one substituent of Z includes an ionic substituent selected from the group consisting of $SO_3^-$, $COO^-$, $PO_3^{2-}$, $O-PO_3^{2-}$, $PO_3R^{31}$, $O-PO_3R^-$ and $N(R^1)_3^+$, wherein R and $R^1$ are aliphatic or aromatic moieties.

6. A composition of matter comprising a photoluminescent compound, the photoluminescent compound having a four-, five-, or six-member aromatic ring Z, with substituents A, B, C, D, E, and F, according to the formula:

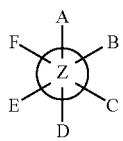

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is =O; when the A substituent is negatively charged, A is —$O^-$;

where each D, E, and F substituent, when present and neutral, is independently selected from the group consisting of =O, =S, =Se, =Te, =N—$R^c$, and =C($R^f$)($R^g$), wherein each of $R^c$ is selected from the group consisting of aliphatic, heteroatom-substituted aliphatic, polyether, aromatic, reactive aliphatic, and reactive aromatic groups, hydrogen, CN, OH, $SO_3H$, and COO—$R^m$, where $R^m$ is selected from a group consisting of hydrogen, aliphatic substituents, aromatic substituents, reactive aliphatic substituents, reactive aromatic substituents, and linked carriers, and where $R^f$ and $R^g$ are selected from the group consisting of carboxylic acid, cyano, carboxamide, carboxylic ester, and aliphatic amine groups, or, alternatively, or in addition, $R^f$ and $R^g$, taken in combination may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —$O^-$, —$S^-$, —$Se^-$, —$Te^-$, —(N—$R^c$)$^-$, and —(C($R^f$)($R^g$))$^-$;

each B and C substituent is selected from the group consisting of $W^1$ and $W^2$, wherein $W^1$ and $W^2$ have the respective formulae

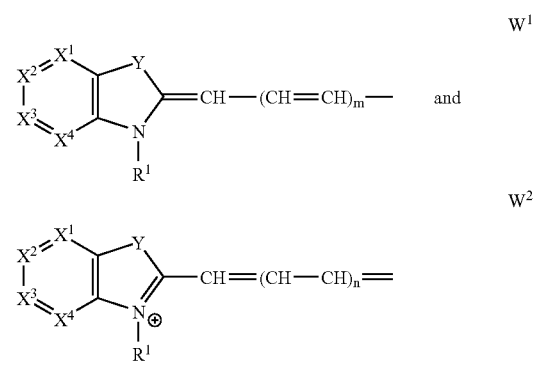

where each B and C substituent is $W^1$ if B and C are adjacent on Z, and one of B and C is $W^1$ and the other of B and C is $W^2$ if B and C are separated by one of A, D, E, and F on ring Z;

m and n are independently selected from the group consisting of 0, 1, and 2;

each Y is independently selected for each of B and C from the group consisting of O, S, N—$R^h$, and C($R^i$)($R^j$), wherein $R^h$ is selected from the group consisting of H, aliphatic groups, alicyclic groups, aromatic groups, spacers bound to ionic and reactive groups, and $R^i$ and $R^j$ are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or $R^i$ and $R^j$ taken in combination form a ring-system that is optionally further substituted by one or more reactive or ionic substituents; provided that at least one Y is C($R^i$)($R^j$) least ne of $R^c$, $R^f$, $R^g$, $R^i$ or $R^j$ includes a reactive group, a linked carrier, or an ionic substituent capable of increasing the hydrophilicity of the entire compound;

each $R^1$ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of N, O, S, and C—$R^k$, wherein $R^k$ is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine;

further comprising a second reporter compound selected from the group consisting of luminophores and chromophores.

7. A composition of matter comprising a fluorescent compound having the formula

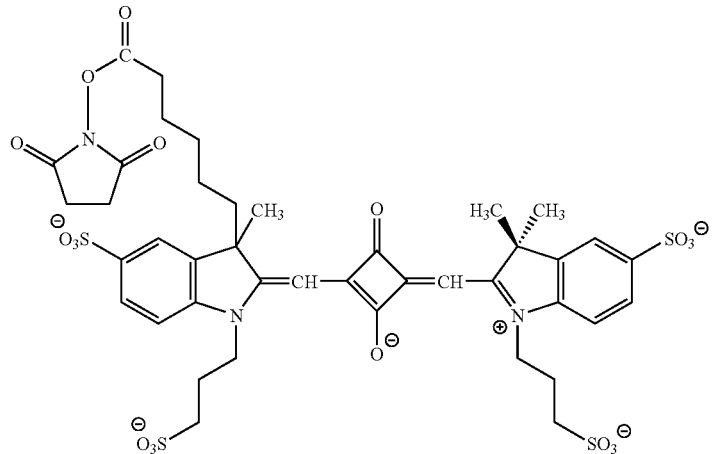

wherein α and β independently are selected from the group consisting of 0, 1, and 2 and $R^7$ is selected from $SO_3^-$, H, and $CH_3$.

8. A composition of matter comprising a compound having the formula

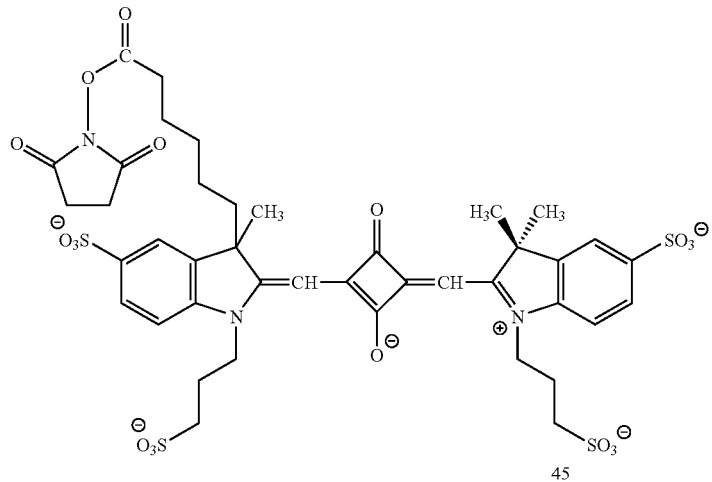

where α and β independently are selected from the group consisting of 0, 1, and 2.

9. A composition of matter comprising a photoluminescent compound having the formula

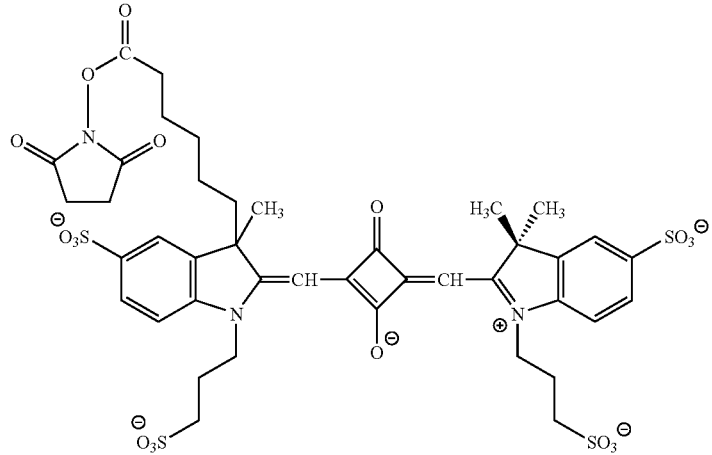

where α and β independently are selected from the group consisting of 0, 1, and 2;

$R^j$ is selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; and $R^7$ is selected from $SO_3^-$, H, and $CH_3$.

10. The composition of claim 6, wherein one of the first and second reporter compounds is an energy transfer acceptor and the other of the first and second reporter compounds is a corresponding energy transfer donor.

11. A protein-conjugate of the compound of claim 7.

12. A protein-conjugate of the compound of claim 9.

13. A composition of matter comprising a photoluminescent compound, the photoluminescent compound having a four-, five-, or six-member aromatic ring Z, with substituents A, B, C, D, E, and F, according to the formula:

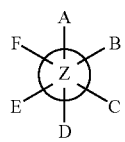

wherein F is absent when Z is a five-member ring, and wherein E and F are absent when Z is a four-member ring;

wherein A, B, C, D, E, and F may be present in any order, provided that B and C are adjacent, in which case each of A, D, E, and F is neutral, or provided that B and C are separated by one of A, D, E, or F, in which case one of A, D, E, and F is negatively charged;

when the A substituent is neutral, A is =O; when the A substituent is negatively charged, A is —O⁻;

where each D, E, and F substituent, when present and neutral, is independently selected from the group consisting of =O, =S, =Se, =Te, =N—$R^c$, and =C($R^f$)($R^g$), wherein each of $R^c$ is selected from the group consisting of aliphatic, heteroatom-substituted aliphatic, polyether, aromatic, reactive aliphatic, and reactive aromatic groups, hydrogen, CN, OH, $SO_3H$, and COO—$R^m$, where $R^m$ is selected from a group consisting of hydrogen, aliphatic substituents, aromatic substituents, reactive aliphatic substituents, reactive aromatic substituents, and linked carriers, and where $R^f$ and $R^g$ are selected from the group consisting of carboxylic acid, cyano, carboxamide, carboxylic ester, and aliphatic amine groups, or, alternatively, or in addition, $R^f$ and $R^g$, taken in combination, may form 5- and 6-membered rings that include, but are not limited to, pyrazolidine-dione, barbituric acid, thiobarbituric acid, isoxazolone, pyrazolone, pyridone, rhodanine, pyrrolotriazole, and pyrazolotriazole rings;

D, E, and F, when present and negatively charged, are independently selected from the group consisting of —O⁻, —S⁻, —Se⁻, —Te⁻, —(N—$R^c$)⁻, and —(C($R^f$)($R^g$))⁻; provided at least one of D, E, and F is —(C($R^f$)($R^g$))⁻;

each B and C substituent is selected from the group consisting of $W^1$ and $W^2$, wherein $W^1$ and $W^2$ have the respective formulae

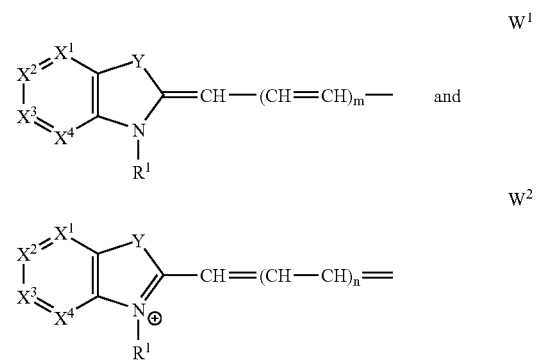

where each B and C substituent is $W^1$ if B and C are adjacent on Z, and one of B and C is $W^1$ and the other of B and C is $W^2$ if B and C are separated by one of A, D, E, and F on ring Z;

m and n are independently selected from the group consisting of 0, 1, and 2;

each Y is independently selected for each of B and C from the group consisting of O, S, N—$R^h$, and C($R^i$)($R^j$), wherein $R^h$ is selected from the group consisting of H, aliphatic groups, alicyclic groups, aromatic groups, spacers bound to ionic and reactive groups, and $R^i$ and $R^j$ are selected from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents and spacers containing one or more ionic substituents capable of increasing the hydrophilicity of the entire compound; or $R^i$ and $R^j$ taken in combination form a ring-system that is optionally further substituted by one or more reactive or ionic substituents; provided that at least one Y is C($R^i$)($R^j$), at least one of $R^c$, $R^f$, $R^g$, $R^i$ or $R^j$ includes a reactive group, a linked carrier, or an ionic substituent capable of increasing the hydrophilicity of the entire compound;

each $R^1$ is independently selected for each of B and C from the group consisting of H, aliphatic groups, alicyclic groups, aromatic groups, polyether groups, linked carriers, reactive groups capable of covalent attachment to a carrier, spacers bound to one or more reactive groups capable of covalent attachment to a carrier, and ionic substituents capable of increasing the hydrophilicity of the entire compound;

each of $X^1$, $X^2$, $X^3$, and $X^4$ is independently selected for each of B and C from the group consisting of N, O, S, and C—$R^k$, wherein $R^k$ is selected from the group consisting of H, F, Cl, Br, I, aliphatic groups, alicyclic groups, aromatic groups, polyether groups, linked carriers, reactive groups capable of covalent attachment to a carrier, spacers bound to one or more reactive groups capable of covalent attachment to a carrier, ionic substituents capable of increasing the hydrophilicity of the entire compound, parts of a condensed aromatic or heterocyclic ring, and parts of a substituted condensed aromatic or heterocyclic ring; and each H may be independently replaced by a fluorine;

the composition further including a metallic nanoparticle, which influences the photophysical properties of the luminescent molecule at a certain distance.

14. The composition of claim 13, wherein binding between the dye-conjugate and the nanoparticle is facilitated via a specific binding pair.

15. The claim of 14, wherein the specific binding pair is selected from the group consisting of antigens and antibodies, ligands and receptors, biotin and streptavidin, lectin and sugar, protein A and antibodies, and oligonucleotides and complementary oligonucleotides.

* * * * *

UNITED STATES PATENT AND TRADEMARK OFFICE
CERTIFICATE OF CORRECTION

PATENT NO. : 7,250,517 B2
APPLICATION NO. : 10/724580
DATED : July 31, 2007
INVENTOR(S) : Ewald A. Terpetschnig, Leonid D. Patsenker and Anatoliy Tatarets It is certified that error appears in the above-identified patent and that said Letters Patent is hereby corrected as shown below:

In Column 13, line 34, please insert --of-- between "versions" and "(13)".

In Claim 5, at Column 57, line 21, please replace "$PO_3R^{31}$" with --$PO_3R^-$--.

In Claim 7, at Column 59, lines 3 - 21, please replace the chemical structure with:

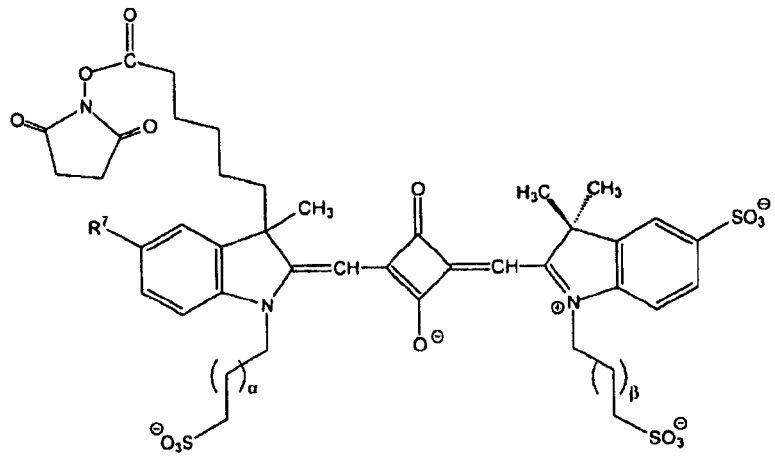

In Claim 8, at Column 59, lines 27 - 46, please replace the chemical structure with:

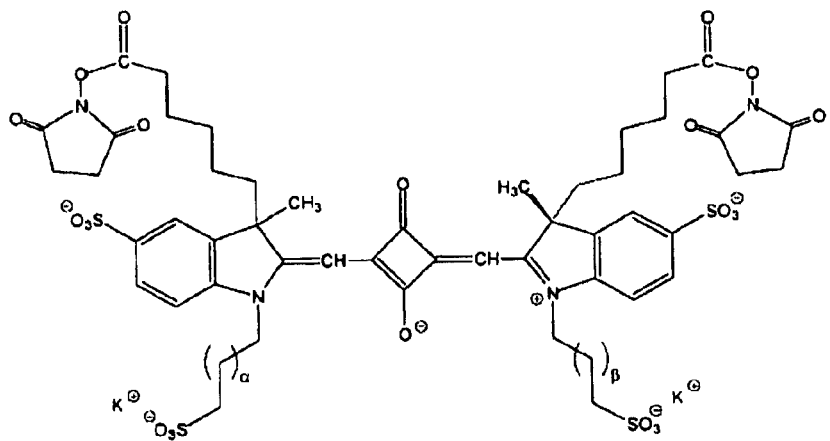

UNITED STATES PATENT AND TRADEMARK OFFICE
CERTIFICATE OF CORRECTION

PATENT NO.         : 7,250,517 B2
APPLICATION NO.    : 10/724580
DATED              : July 31, 2007
INVENTOR(S)        : Ewald A. Terpetschnig, Leonid D. Patsenker and Anatoliy Tatarets It is certified that error appears in the above-identified patent and that said Letters Patent is hereby corrected as shown below:

In Claim 9, at Column 59, lines 51 - 67, please replace the chemical structure with:

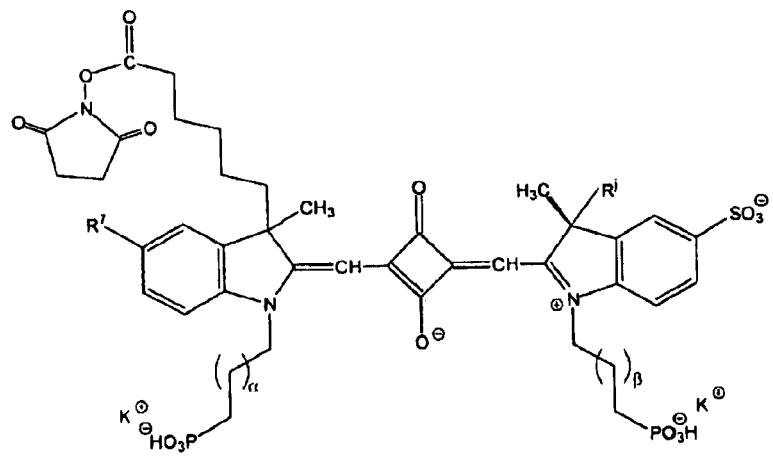

Signed and Sealed this

Third Day of June, 2008

JON W. DUDAS
*Director of the United States Patent and Trademark Office*